(12) United States Patent
Wisbey et al.

(10) Patent No.: US 10,420,474 B2
(45) Date of Patent: Sep. 24, 2019

(54) SYSTEMS AND METHODS FOR GATHERING AND INTERPRETING HEART RATE DATA FROM AN ACTIVITY MONITORING DEVICE

(71) Applicant: LOGITECH EUROPE, S.A., Lausanne (CH)

(72) Inventors: Ben Wisbey, Canberra (AU); Hagen Diesterbeck, Coromandel (NZ); Stephen Duddy, Moama (AU)

(73) Assignee: LOGITECH EUROPE, S.A., Lausanne (CH)

( * ) Notice: Subject to any disclaimer, the term of this patent is extended or adjusted under 35 U.S.C. 154(b) by 270 days.

(21) Appl. No.: 15/012,809

(22) Filed: Feb. 1, 2016

(65) Prior Publication Data

US 2017/0215742 A1    Aug. 3, 2017

(51) Int. Cl.
*A61B 5/0205* (2006.01)
*A61B 5/11* (2006.01)
(Continued)

(52) U.S. Cl.
CPC .......... *A61B 5/0205* (2013.01); *A61B 5/0022* (2013.01); *A61B 5/117* (2013.01);
(Continued)

(58) Field of Classification Search
CPC .......................... A61B 5/02405; A61B 5/0205
See application file for complete search history.

(56) References Cited

U.S. PATENT DOCUMENTS 2,189,096 A    2/1940 Alonge
3,543,724 A    12/1970 Kirkpatrick et al.
(Continued)

OTHER PUBLICATIONS

"Watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).
(Continued)

*Primary Examiner* — George R Evanisko
(74) *Attorney, Agent, or Firm* — Joseph J. Stevens

(57) ABSTRACT

Systems and methods are provided for gathering and generating heart rate data to determine the user's current physical condition. On such system include a wearable device having a bio sensor that measures biometrics and a motion sensor that monitors activity. The system also includes a processor coupled to the bio sensor and the motion sensor, and a transitory computer-readable medium operatively coupled to the processor and storing instructions that, when executed, cause the processor to execute specific functions. The instructions are executed to cause the processor to generate biometric data when executed, cause the processor to execute specific functions. The instructions are executed to cause the processor to generate heart rate data from the biometrics measured by the bio sensor, generate motion data from the activity monitored by the motion sensor, calculate heart rate variability (HRV) data from the biometrics measured by the bio sensor, and determine the current state of the user's physical condition based on the correlation of one or more of the heart rate data, motion data, and calculated HRV data gathered.

15 Claims, 15 Drawing Sheets

(51) Int. Cl.
*A61B 5/00* (2006.01)
*A61B 5/117* (2016.01)
*G06F 19/00* (2018.01)
*G16H 40/67* (2018.01)

(52) U.S. Cl.
CPC ............ *A61B 5/1118* (2013.01); *A61B 5/681* (2013.01); *A61B 5/6803* (2013.01); *A61B 5/7271* (2013.01); *G06F 19/00* (2013.01); *G16H 40/67* (2018.01)

(56) References Cited

U.S. PATENT DOCUMENTS

| | | | |
|---|---|---|---|
| 3,978,849 | A | 9/1976 | Geneen |
| 4,129,124 | A | 12/1978 | Thalmann |
| 4,224,984 | A | 9/1980 | Cramer et al. |
| 4,307,727 | A | 12/1981 | Haynes |
| 4,331,154 | A | 5/1982 | Broadwater et al. |
| 4,407,295 | A | 10/1983 | Steuer et al. |
| 4,409,983 | A | 10/1983 | Albert |
| 4,491,970 | A | 1/1985 | Lawhite et al. |
| 5,301,154 | A | 4/1994 | Suga |
| 5,392,261 | A | 2/1995 | Hsu |
| 5,406,952 | A | 4/1995 | Barnes et al. |
| 5,524,637 | A | 6/1996 | Erickson |
| 5,734,625 | A | 3/1998 | Kondo |
| 5,755,623 | A | 5/1998 | Mizenko |
| 5,899,370 | A | 5/1999 | Bould |
| 6,151,968 | A | 11/2000 | Chou |
| 6,361,503 | B1 | 3/2002 | Starobin et al. |
| 6,736,759 | B1 | 5/2004 | Stubbs et al. |
| 7,192,401 | B2 | 3/2007 | Saalasti et al. |
| 7,717,827 | B2 | 5/2010 | Kurunmaki et al. |
| 7,914,425 | B2 | 3/2011 | Hanoun |
| 8,992,385 | B2 | 3/2015 | Lemos |
| 9,044,149 | B2 * | 6/2015 | Richards ............ A61B 5/02427 |
| 9,579,060 | B1 * | 2/2017 | Lisy ..................... A61B 5/6803 |
| 2002/0151811 | A1 | 10/2002 | Starobin et al. |
| 2002/0188210 | A1 | 12/2002 | Aizawa |
| 2003/0065269 | A1 | 4/2003 | Vetter et al. |
| 2005/0056655 | A1 | 3/2005 | Gary |
| 2005/0116811 | A1 | 6/2005 | Eros et al. |
| 2005/0256416 | A1 | 11/2005 | Chen |
| 2006/0183980 | A1 | 8/2006 | Yang |
| 2007/0118043 | A1 | 5/2007 | Oliver et al. |
| 2008/0132383 | A1 | 6/2008 | Einav et al. |
| 2008/0228089 | A1 | 9/2008 | Cho et al. |
| 2009/0312656 | A1 | 12/2009 | Lau et al. |
| 2010/0197463 | A1 | 8/2010 | Haughay, Jr. et al. |
| 2011/0021319 | A1 | 1/2011 | Nissila et al. |
| 2011/0092790 | A1 | 4/2011 | Wilder-Smith et al. |
| 2011/0260870 | A1 | 10/2011 | Bailey |
| 2012/0022341 | A1 | 1/2012 | Zdeblick |
| 2012/0168471 | A1 | 7/2012 | Wilson |
| 2012/0253485 | A1 | 10/2012 | Weast et al. |
| 2013/0064049 | A1 | 3/2013 | Pileri et al. |
| 2013/0237778 | A1 | 9/2013 | Rouquette |
| 2014/0032234 | A1 | 1/2014 | Anderson |
| 2014/0073486 | A1 * | 3/2014 | Ahmed ............... A61B 5/02405 482/9 |
| 2014/0107493 | A1 | 4/2014 | Yuen et al. |
| 2014/0228175 | A1 | 8/2014 | Lemos et al. |
| 2015/0173631 | A1 * | 6/2015 | Richards ............ A61B 5/02427 600/479 |
| 2015/0251074 | A1 * | 9/2015 | Ahmed ............... A61B 5/02405 700/91 |
| 2016/0007864 | A1 * | 1/2016 | Scharf .................. A61B 5/6814 600/301 |
| 2016/0007934 | A1 * | 1/2016 | Arnold ................. A61B 5/1123 600/595 |
| 2016/0058378 | A1 * | 3/2016 | Wisbey .............. A61B 5/02405 600/479 |
| 2017/0065224 | A1 * | 3/2017 | Rahko .................. A61B 5/7435 |
| 2017/0188851 | A1 * | 7/2017 | LeBoeuf .................. A61B 5/00 |
| 2017/0231490 | A1 * | 8/2017 | Toth ......................... A61B 5/40 600/558 |

OTHER PUBLICATIONS

"Elite Clock Military Style LED Watch" by ledwatchsuk. YouTube [dated May 31, 2011][online][retrieved on Aug. 14, 2015].

* cited by examiner

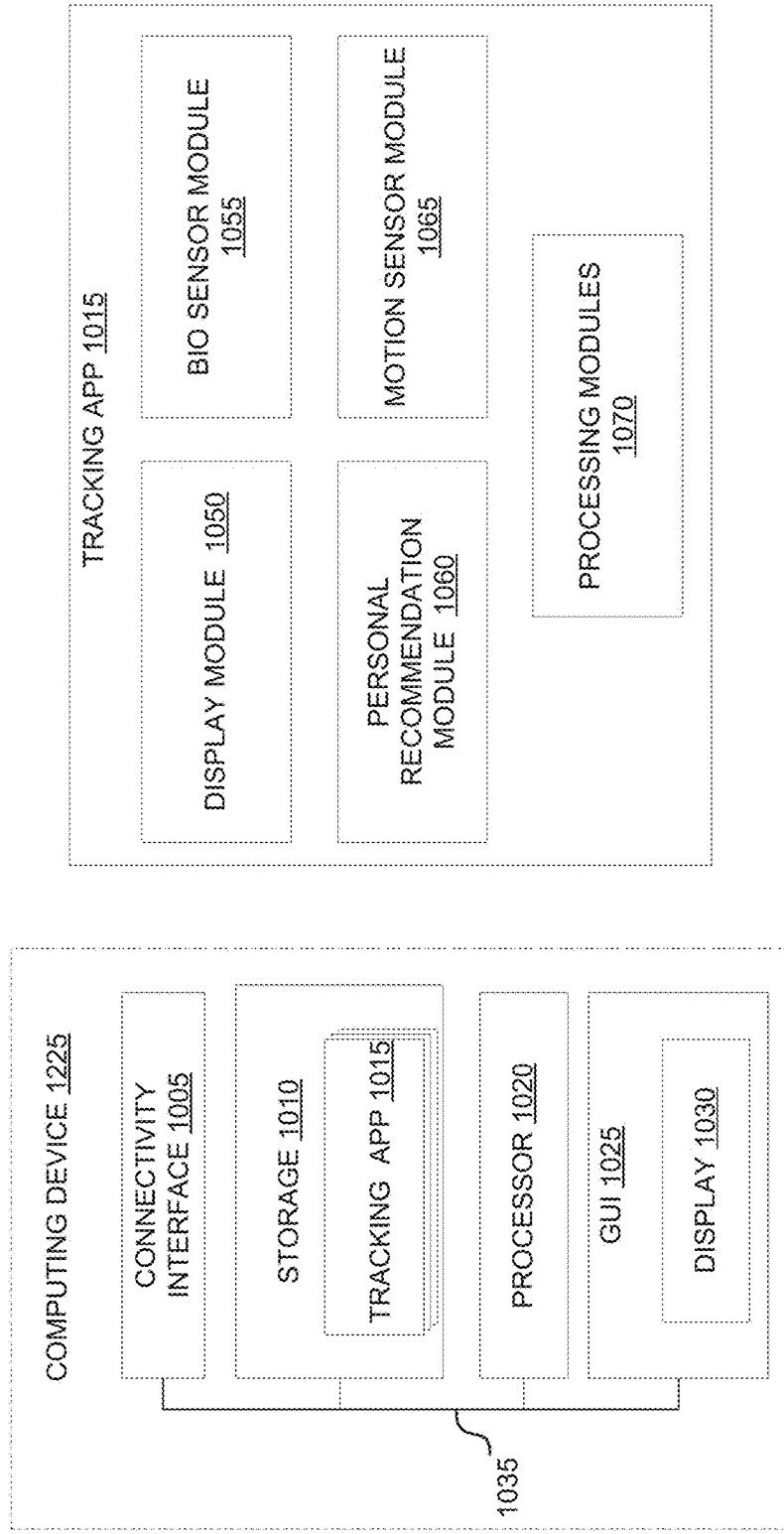

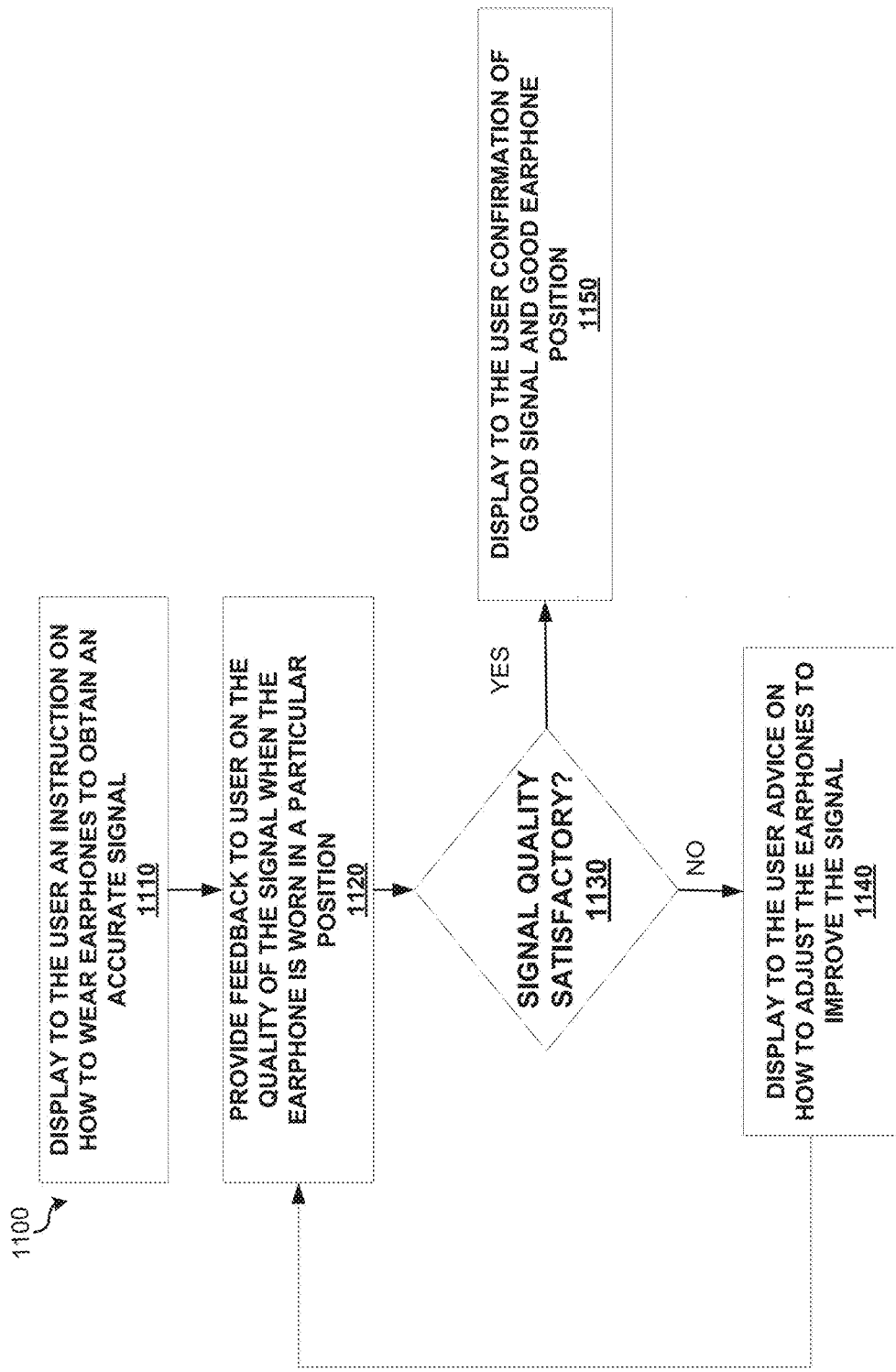

SYSTEMS AND METHODS FOR GATHERING AND INTERPRETING HEART RATE DATA FROM AN ACTIVITY MONITORING DEVICE

TECHNICAL FIELD

The present disclosure relates to fitness and activity monitoring devices. More particularly, the present disclosure is directed to systems, methods, and devices, for gathering and interpreting heart rate data to determine a user's physical condition.

BACKGROUND

Conventional activity monitoring and fitness tracking devices that monitor heart rate, fail to provide constructive information that informs the user of his or her current physical state or condition based on the gathered heart rate data. Rather, currently available solutions only seek to passively monitor heart rate data to determine the user's activity and response to the same. As such, current solution do not provide information about a user's current physical state or condition that may allow the user to make personal improvements or constructive changes to his or her overall fitness and well-being based on the heart rate data gathered from the activity monitoring devices.

BRIEF SUMMARY OF THE DISCLOSURE

In view of the above shortcomings in conventional fitness monitoring devices, there exists a long-felt need for activity monitoring devices that takes into account one or more of biometric data and movement data. In particular, there exists a need for fitness monitoring devices that enable monitoring a user's movement and heart rate data in order to accurately determine the user's current physical condition. In this manner, the user can be made aware of his or her current physical state or condition and make better activity and personal choices to create a more balanced and healthier lifestyle.

In one embodiment, a system for determining a user's physical condition includes a processor; a heartrate sensor electrically coupled to the processor; and a motion sensor electrically coupled to the processor, where the processor is configured to process electronic input signals from the motion sensor and the heartrate sensor. In this embodiment, the system is configured to generate heart rate data from the biometrics measured by the bio sensor; generate motion data from the activity monitored by the motion sensor; calculate heart rate variability (HRV) data from the biometrics measured by the bio sensor; and determine a current state of the user's physical condition based on a correlation of one or more of the heart rate data, motion data, and HRV data gathered. In some implementations of the embodiment, the correlation of the motion data, heart rate data, and HRV data determines if the user is stressed, relaxed, recovering, or exercising.

Other features and aspects of the disclosed method and system will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The present disclosure, in accordance with one or more various embodiments, is described in detail with reference to the following Figures. The Figures are provided for purposes of illustration only and merely depict typical or example embodiments of the disclosure.

FIG. 10A is a block diagram of an example computing device, in accordance with various embodiments.

FIG. 10B illustrates an example application and modules, in accordance with various embodiments.

FIG. 11 is an operational flow diagram illustrating a method of prompting a user to adjust the placement of earphones in the user's ear, in accordance with various embodiments described herein.

DETAILED DESCRIPTION

Embodiments of the present disclosure are directed to systems, methods, and devices, capable of determining a user's overall physical condition based on the gathered heart rate data. The details of some example embodiments of the systems, methods, and devices of the present disclosure are set forth in the description below. Other features, objects, and advantages of the disclosure will be apparent to one of skill in the art upon examination of the present description, figures, examples, and claims. It is intended that all such additional systems, methods, features, and advantages be included within this description, be within the scope of the present disclosure, and be protected by one or more of the accompanying claims.

Figure 1:
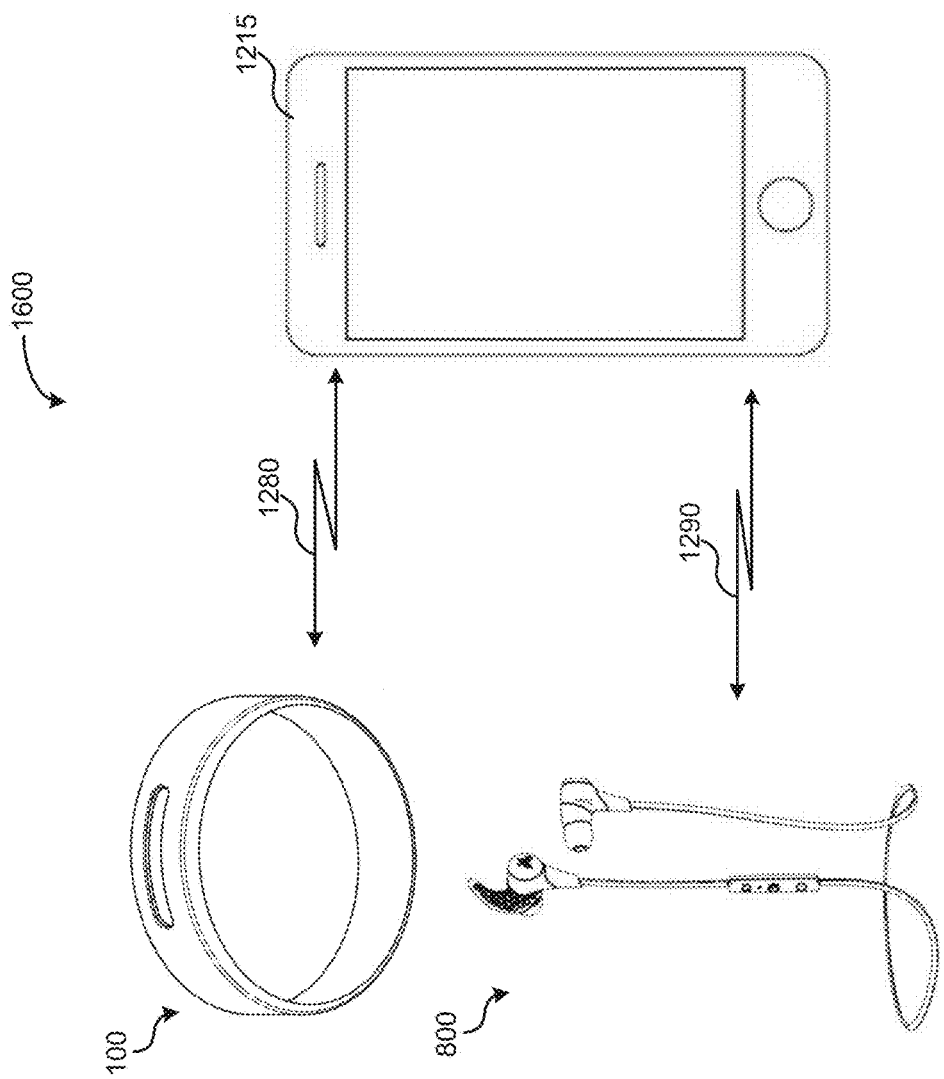
FIG. 1 illustrates an example communications environment in which embodiments of the disclosure may be implemented.

FIG. 1 depicts example communication environment 1600, which may be used in connection with implementing embodiments of the disclosed systems, methods, and devices. As shown, communications environment 1600 may include a band 100 and earphones 800. As will be described in detail herein, band 100 and earphones 800 may be used to monitor activity and/or measure biometrics. Additionally, band 100 and earphones 800 may be coupled to computing device 1215, which in the illustrated example is a mobile device. This coupling may be implemented in some examples using links 1280 and 1290, which in various instances may be a wired or wireless connection.

Computing device 1215 may collect additional information from the user, such as biometrics and activity information that may be used to supplement or that may be used in place of information received from band 100 or earphones 800. Computing device 1215 may include a variety of electronic computing devices, such as, for example, a smartphone, tablet, laptop, and the like. In such cases, computing device 1215 may be configured to receive biometrics and/or activity information over links 1280 and 1290. Furthermore, computing device 1215 may include a graphical user interface (GUI) for displaying and interacting with one or more of band 100 and/or earphones 800, including by interacting with data collected by and received from band 100 and/or earphones 800, and by controlling the operation of band 100 and/or earphones 800.

Here it will be noted that the GUI of computing device 1215 may additionally perform functions such as accepting user input and displaying processed biometric and activity data to the user. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, links 1280 and 1290 may be based on one or more wireless communication protocols such as Bluetooth, ZigBee, 802.11 protocols, Infrared (IR), Radio Frequency (RF), 2G, 3G, 4G, etc.

Figure 2:
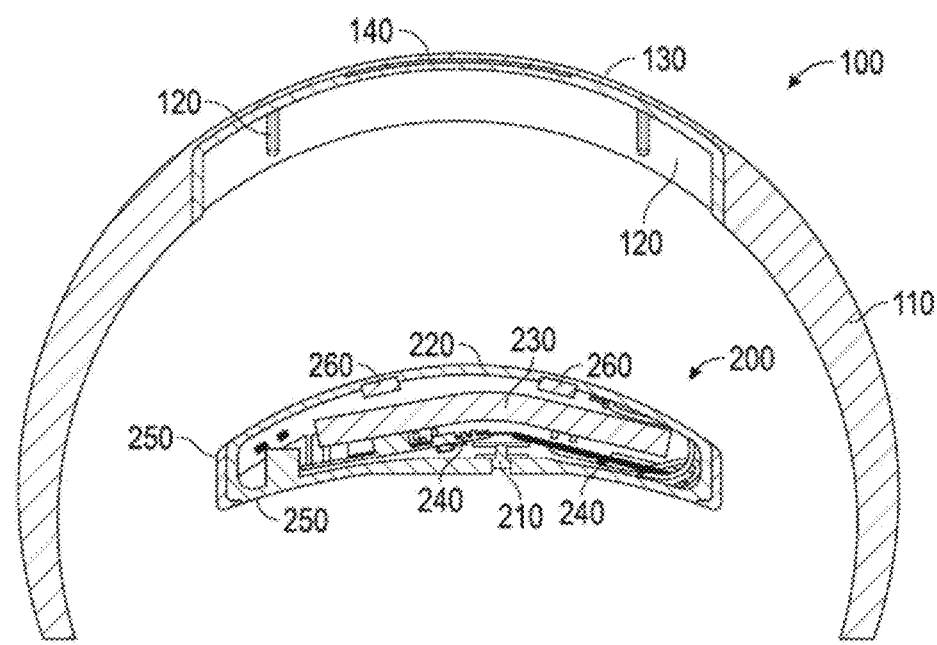
FIG. 2 illustrates a cross-sectional view of an example band that may be used to implement embodiments of the disclosure.
Figure 3:
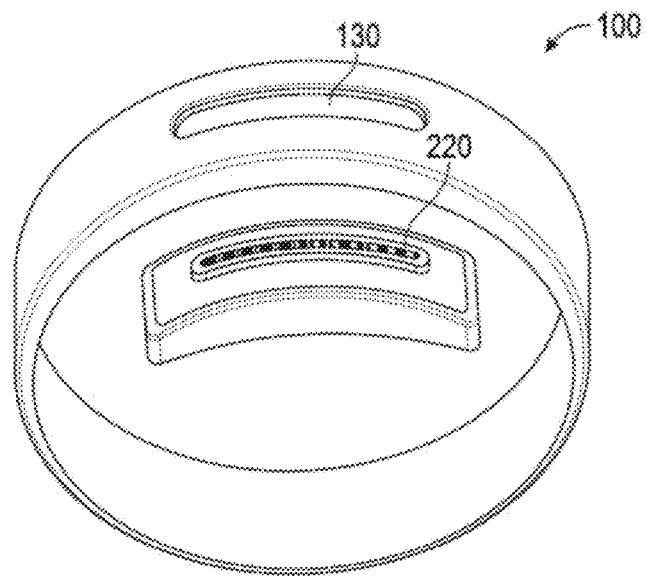
FIG. 3 illustrates a perspective view of the example band, in accordance with various embodiments.

FIG. 2 depicts an exploded cross-sectional view of example embodiments of band 100. FIG. 3 illustrates a perspective view of band 100. Aspects of FIGS. 2 and 3 will now be described together. As depicted, band 100 includes band portion 110 and electronic capsule 200, which includes various electronic components embodied therein. Electronic capsule 200 is a removable/detachable component that may be coupled to and removable/detachable from band portion 110. This may be accomplished in a variety of ways, e.g., magnetic attraction forces, snap-fit/friction, etc. In other cases, electronic capsule 200 may be integrally formed with band portion 110.

Electronic capsule 200 may include various components, such as battery 230, logic circuits 240, casing 250, and one or more of wrist bio sensor 210, finger bio sensor 220, and/or a motion sensor (e.g., accelerometer, gyroscope, magnetometer, or other inertial measurement unit). Typically, at least one of wrist bio sensor 210 and finger bio sensor 220 is a heart rate sensor configured to detect the heart rate of a wearer of band 100. In the illustrated embodiment, finger bio sensor 220 protrudes outwardly from a first side (i.e., the top) of casing 250, and wrist biosensor protrudes outwardly from a second side (i.e., the bottom) of casing 250. As depicted, aperture 130 of band portion 110 substantially matches the dimensional profile of finger bio sensor 220, such that finger bio sensor 220 may be exposed and accessible to the touch of a user's finger through aperture 130 when band 100 is worn by the user. In various embodiments, battery 230, logic circuits 240, and an optional motion sensor are enclosed inside of casing 250. Battery 230 is electronically coupled and supplies power to logic circuits 240. By way of example, logic circuits 240 may by implemented using printed circuit boards (PCBs). Although band 100 is shown in FIGS. 2 and 3 as including both wrist biosensor 210 and finger bio sensor 220, some embodiments include only one or the other.

Casing 250 may be made of various materials known in the art, including, for example, molded plastic, silicone, rubber, or another moldable material. Additionally, casing 250 may be sealing using an ultrasonic welding process to be substantially water tight, thus protecting electronic capsule 200 from the elements. Further, band 100 may be configured to encircle (either partially as in FIG. 2, or entirely as in FIG. 3) a wrist or other limb (e.g., ankle, etc.) of a human or other animal or object. In one embodiment, band 100 is adjustable in size/fit. In some embodiments, cavity 120 is notched on the radially inward facing side of band 100 and shaped to substantially the same dimensions as the profile of electronic capsule 200. In addition, aperture 130 may be located in the material of band 100 within cavity 120. Aperture 130 may be shaped to substantially the same dimensions as the profile of the finger biosensor 220. As shown, cavity 120 and aperture 130 are in combination designed to detachably couple to electronic capsule 200 such that, when electronic capsule 200 is positioned inside cavity 120, finger biosensor 220 protrudes at least partially into aperture 130 such that electronic capsule 200 may be exposed to the touch of a user's finger. Electronic capsule 200 may further include one or more magnets 260 configured to secure electronic capsule 200 in cavity 120. Magnets 260 may be concealed in casing 250. Alternatively, cavity 120 may be configured to conceal magnets 260 when electronic capsule 200 detachably couples in cavity 120 and aperture 130.

Wristband 100 may further include a ferromagnetic metal strip 140 concealed in band portion 110 within cavity 120. In such a case, when electronic capsule 200 is positioned within cavity 120, magnets 260 are attracted to ferromagnetic strip 140 and pull electronic capsule 200 radially outward with respect to band portion 110. The force provided by magnets 260 may detachably secure electronic capsule 200 inside cavity 120. In alternative embodiments, electronic capsule 200 may be positioned inside cavity 220 and be affixed therein using a form-fit, press-fit, snap-fit, friction-fit, VELCRO, or other temporary adhesion or attachment technology.

In some embodiments, logic circuits 240 include a motion sensor that includes an inertial measurement unit (e.g., one or more of a gyroscope, accelerometer, and magnetometer, etc.), a wireless transmitter, and additional circuitry. Logic circuits 240 may be configured to process electronic signals from bio sensors (e.g., finger bio sensor 220 and wrist bio sensor 210) and/or motion sensors, convert/store the electronic signals as data, and output the data via the transmitter (e.g., using wireless protocols described herein). In other scenarios, this data may be output using a wired connection (e.g., USB, fiber optic, HDMI, or the like).

Referring again to electronic capsule 200, in some embodiments, the electronic signals processed by logic circuits 240 include an activation time signal and a recovery time signal. In these embodiments, logic circuits 240 may process the electronic signals to calculate an activation recovery interval equal to the difference between the activation time signal and the recovery time signal. The electronic of signals may include heart rate information collected by and received from one or more of the wrist biosensor 210 and finger biosensor 220. Further still the electronic signals may include electro-cardio signals from a user's heart. In these embodiments, logic circuits 240 may process the electro-cardio signals to calculate and store a RR-interval and determine a heart rate. The RR-interval may be the delta in time between two R-waves, where the R-waves are the electro-cardio signals generated by a ventricle contraction in the heart. The RR-interval may further be used to calculate and store a heart rate variability (HRV) value that indicates the variation over time of the time delta between consecutive heartbeats. In some embodiments, logic circuits 240 may convey the electronic signals to, e.g., computing device 1215, by a transmitter, such that computing device 1215 may perform various calculations (e.g., of HRV).

In some instances, finger bio sensor 220 and wrist bio sensor 210 may be replaced or supplemented by a single bio sensor configured to detect and measure biometric information. The single bio sensor may be an optical bio sensor such as a pulse oximeter configured to detect blood oxygen saturation levels. The pulse oximeter may output an electronic signal to logic circuits 240 indicating a detected cardiac cycle phase and/or heart rate, and logic circuits 240 may use such information (e.g. the cardiac cycle phase data) to further calculate an HRV value, or logic circuits 240 may convey the information to, e.g., computing device 1215, by a transmitter, such that computing device 1215 may perform various calculations (e.g., of HRV). Logic circuits 240, in some deployments, may further detect and store metrics based on motion detection, such as the amount of physical activity, sleep, or rest over a period of time, or the amount of time with or without physical activity over a period of time.

Figure 4:
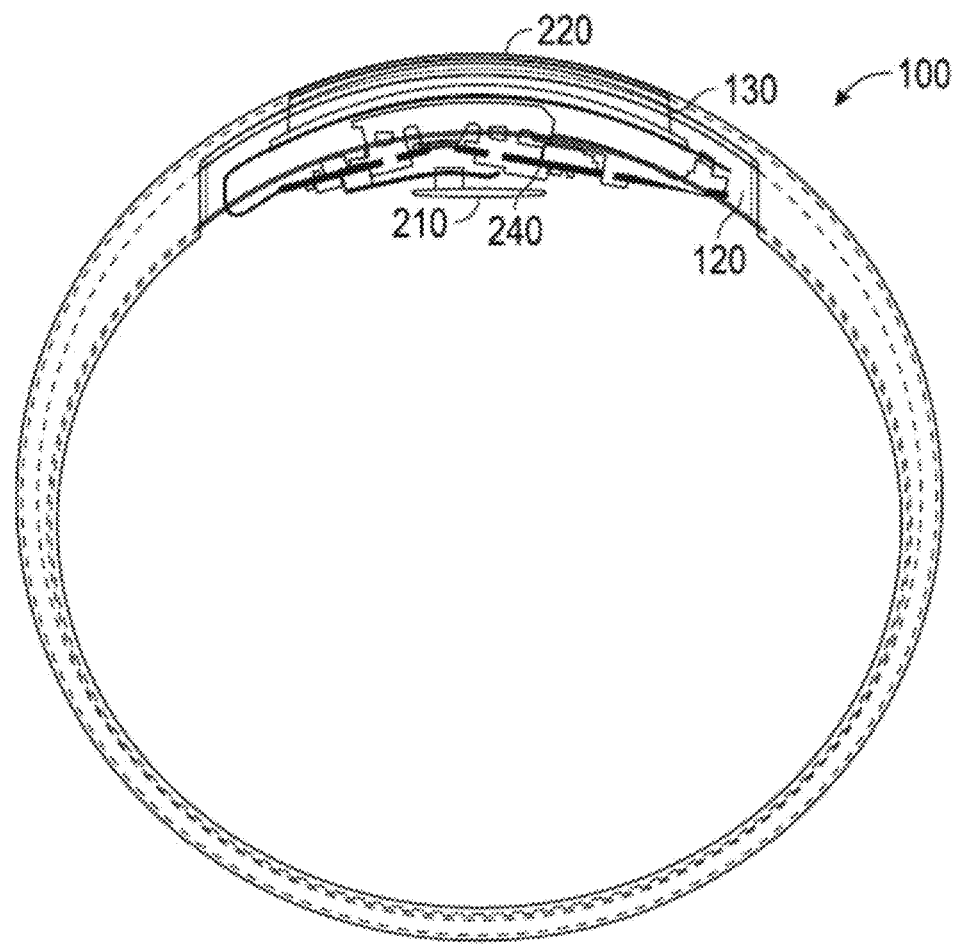
FIG. 4 illustrates a cross-sectional view of an example electronic capsule that may be used in connection with the example band, in accordance with various embodiments.

FIG. 4 illustrates a cross-sectional view of one embodiment of band 100 when assembled with electronic capsule 200. In this embodiment, electronic capsule 200 is positioned inside cavity 120 such that finger biosensor 220 is partially disposed in and exposed through aperture 130. Wrist biosensor 210 protrudes from the radially inward facing side band portion 110. In this configuration, wrist biosensor 210 may contact the skin on the wearer's limb when the band 100 is worn.

Figure 5:
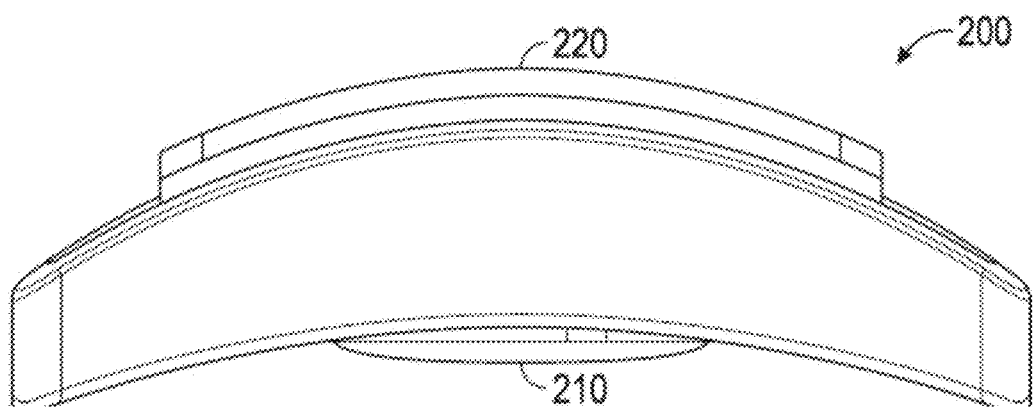
FIG. 5 illustrates a side view of the example electronic capsule, in accordance with various embodiments.

FIG. 5 illustrates a side view of electronic capsule 200. As depicted, finger biosensor 220 may protrude from a first side of electronic capsule 200, and wrist biosensor 210 may protrude from a second side of electronic capsule 200. Casing 250 encloses components of electronic capsule 200. Casing 250 may include moldable plastic. Alternatively, casing 250 may include metal, rubber, composite material, or another, moldable material. In one embodiment, casing 250 is ultrasonically welded together to make the casing water tight and/or resistant. In alternative embodiments, other methods may be used to make the casing water tight/resistant.

Figure 6:
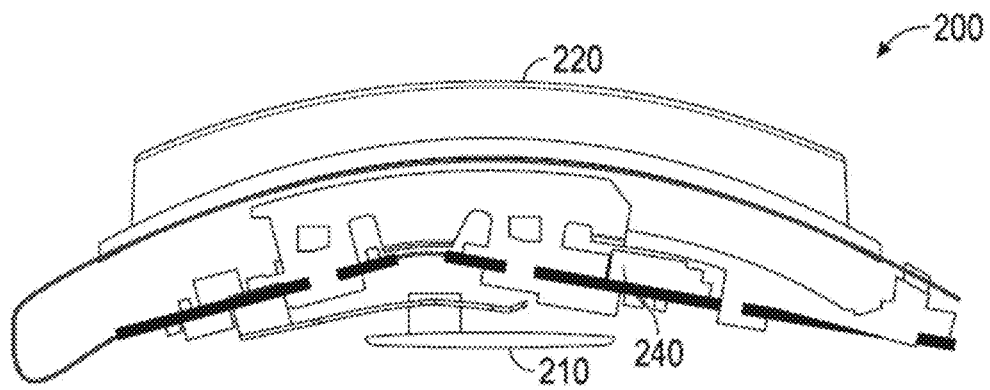
FIG. 6 illustrates a cross-sectional view of the example electronic capsule, in accordance with various embodiments.

FIG. 6 illustrates another cross-sectional view of electronic capsule 200. In the illustrated embodiment, finger biosensor 220 protrudes from a first side of electronic capsule 200, and wrist biosensor 210 protrudes from a second side of electronic capsule 200. Both finger biosensor 220 and wrist biosensor 210 are electronically coupled to logic circuits 240.

Figure 7:
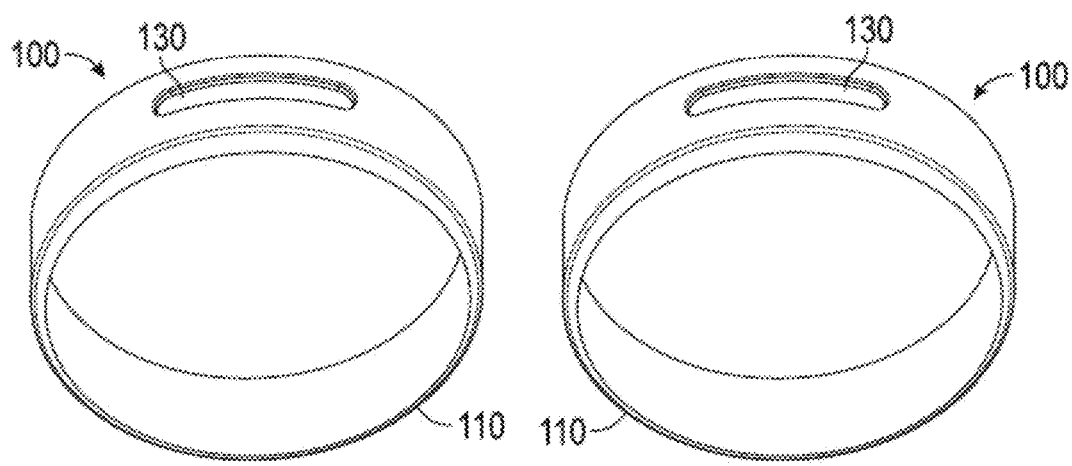
FIG. 7 illustrates a perspective view of the example band, in accordance with various embodiments.

FIG. 7 is a perspective view of two possible variants of band 100 that may be used in accordance with embodiments disclosed herein. Each band 100 in this embodiment includes flexible material, and aperture 230 is disposed on each band 100. Each electronic capsule 200 may be sized so as to be easily removed from one band 100 and placed in another band 100. Bands 100 may also be constructed with different dimensions, including different diameters, widths, and thicknesses, in order to accommodate different sized/shaped limbs and appendages, as well as wearer preferences. In one embodiment, bands 100 may be adjustable to accommodate different sizes/shapes of limbs. Further, bands 100 may be made in different colors, and different flexible materials, such as silicone, plastic, metal chain links, composite material, leather, synthetic leather, fabric, or other flexible materials.

In some embodiments electronic capsule 300 may be detachably coupled to various other locations besides band 100. For example, electronic capsule 300 may be attached to a user's shoe and/or sock, coupled to sports equipment (e.g. the handle of a racket or bicycle) such that one of bio sensors 310 or 320 may contact parts of a user's body.

Electronic capsules 200 used in accordance with some embodiments of the presently disclosed technology may include one or more optical sensors such as a heart rate sensor or oximeter. For example, the oximeter may sense heart rate and/or HRV by detecting blood oxygenation level changes as changes in coloration at the surface of a user's skin. The optical sensor may be positioned to face radially inward towards a limb when band 100 is worn. Alternatively, the optical sensor may be separate from electronic capsule 200, but still detachably coupled to band 100 and/or electronically coupled to circuit boards that may be enclosed in electronic capsule 200 (e.g., wireless coupled or otherwise).

Referring again to FIG. 1, in various embodiments, computing device 1215 may receive, process and/or display data collected, determined, and/or processed by logic circuits 240, thereby allowing the user to interact with band 100 and/or otherwise monitor the user's activity and/or biometrics, as will be further described herein. Additionally, computing device 1215 may be used to collect additional activity monitoring data using sensors (e.g. bio sensors, motion sensors, etc.) included in computing device 1215. Further still, computing device 1215 may be bi-directionally communicatively coupled (e.g., by links 1280 and 1290) with band 100 such that computing device 1215 may be used to configure the functionality of logic circuits 240. In such cases, logic circuits 140 include a receiver as well as a transmitter.

In other embodiments, computing device 1215 may connect to the Internet and receive biometric and/or activity data gathered by band 100 over a web browser. For example, the band 100 may gather/process biometric, activity, and other data, and transmit that data to a remote file server, such that computing device 1215 may then access the data from the remote file server without directly linking to band 100. In yet further embodiments, computing device 1215 may be mechanically coupled, electrically coupled, or both mechanically and electrically coupled to band 100, such that communication can take place over a wired or near-field connection.

Figure 8A:
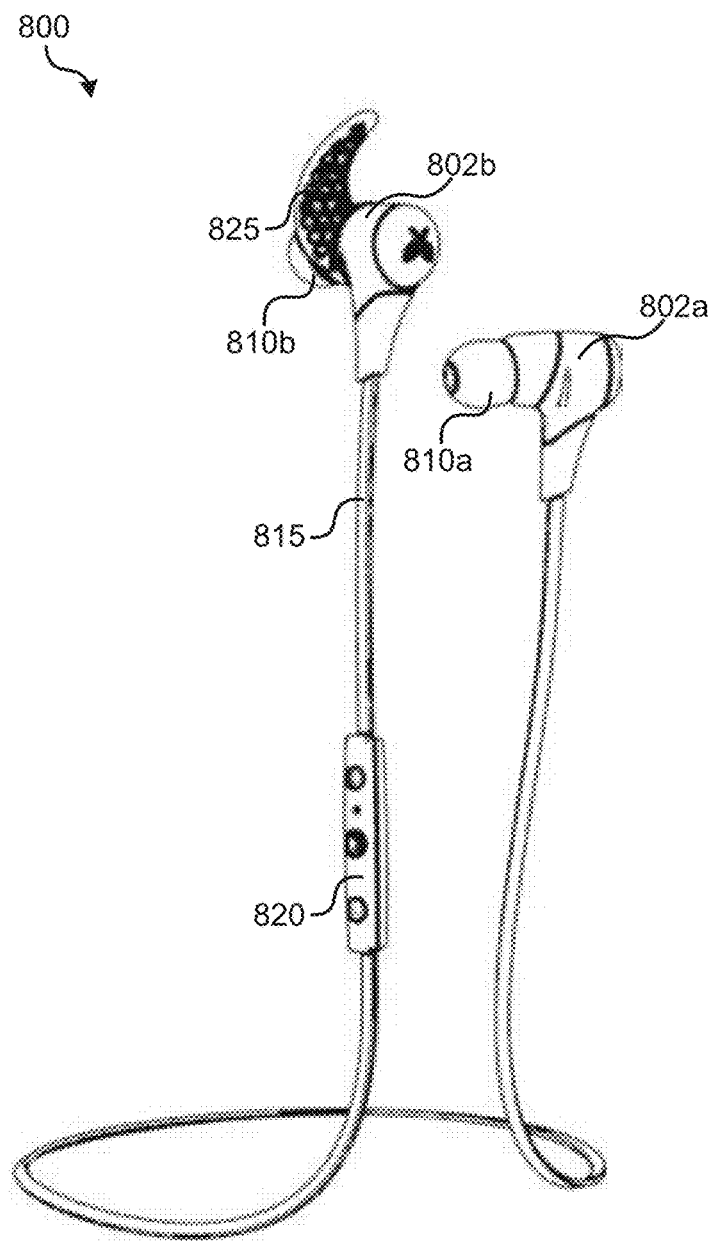
FIG. 8A illustrates a perspective view of an example earphones, in accordance with various embodiments.

FIG. 8A illustrates a perspective view of earphones 800. FIG. 8A will generally be described in conjunction with FIG. 8B, which illustrates an example architecture of circuitry that may be used to implement earphones 800. Earphones 800 include earphone 802a, which may correspond to a wearer's right ear, and earphone 802b, which may correspond to a wearer's left ear. Generally, the aspects described herein with respect to earphone 802a may apply equally to earphone 802b, and vice versa. As shown in FIG. 8A, earphones 802a and 802b include respective tips 802a and 802b. Earphones 800 also include controller 820 and cable 815. Cable 815 electrically couples earphones 802a and 802b to one another, and also couples earphones 802a, 802b to controller 820. Additionally, earphones 802a, 802b may in some cases include fin 825 that contacts folds in the outer ear anatomy of the wearer in order to further secure the earphones 802a and/or 802b to the wearer's ear.

Earphones 800 may be constructed to have dimensions, including different diameters, widths, and thicknesses, in order to accommodate different human or animal ear sizes and different preferences. In some embodiments of earphones 800, the housing of each earphone 802a and 802b is a rigid shell that surrounds electronic components within. In some deployments, these electronic components may include components described above with respect to electronic capsule 200. In other embodiments, referring now to FIG. 8B, examples of the electronic components include motion sensor 835, optical heartrate sensor 830, audio-electronic components such as drivers 870a, 870b and speakers 805a, 805b, and other circuitry (e.g., processor 845 and memories 840, 855). One or more of these components may optionally reside outside of earphones 802a, 802b, for example, in controller 820 or elsewhere. The rigid shell of the housing may be made with plastic, metal, rubber, or other materials known in the art. The housing may be cubic shaped, prism shaped, tubular shaped, cylindrical shaped, or otherwise shaped to house the electronic components or to fit well within a wearer's ear.

Referring back to FIG. 8A, tips 810a, 810b may be rounded, parabolic, and/or semi-spherical, so as to comfortably and securely fit within a wearer's ear, with the distal end of tip 810a, 810b contacting an outer rim of the wearer's outer ear canal. In some embodiments, tip 810a, 810b is removable so as to be exchanged with alternate tips of varying dimensions, colors, or designs to accommodate a wearer's preference and/or fit more closely match the radial profile of the wearer's outer ear canal. Tip 810a, 810b may be made with softer materials such as rubber, silicone, fabric, or other materials as would be appreciated by one of ordinary skill in the art upon studying the present disclosure.

Controller 820 may provide various controls (e.g., buttons and switches) related to media playback, such as, for example, volume adjustment, track skipping, audio track pausing, and the like. Additionally, controller 820 may include various controls related to the gathering of biometrics and/or activity information, such as, for example, controls for enabling or disabling heart rate and motion detection. Controller 820 may be of a simple design having, for example, three buttons to perform various of the controls described herein.

Figure 8B:
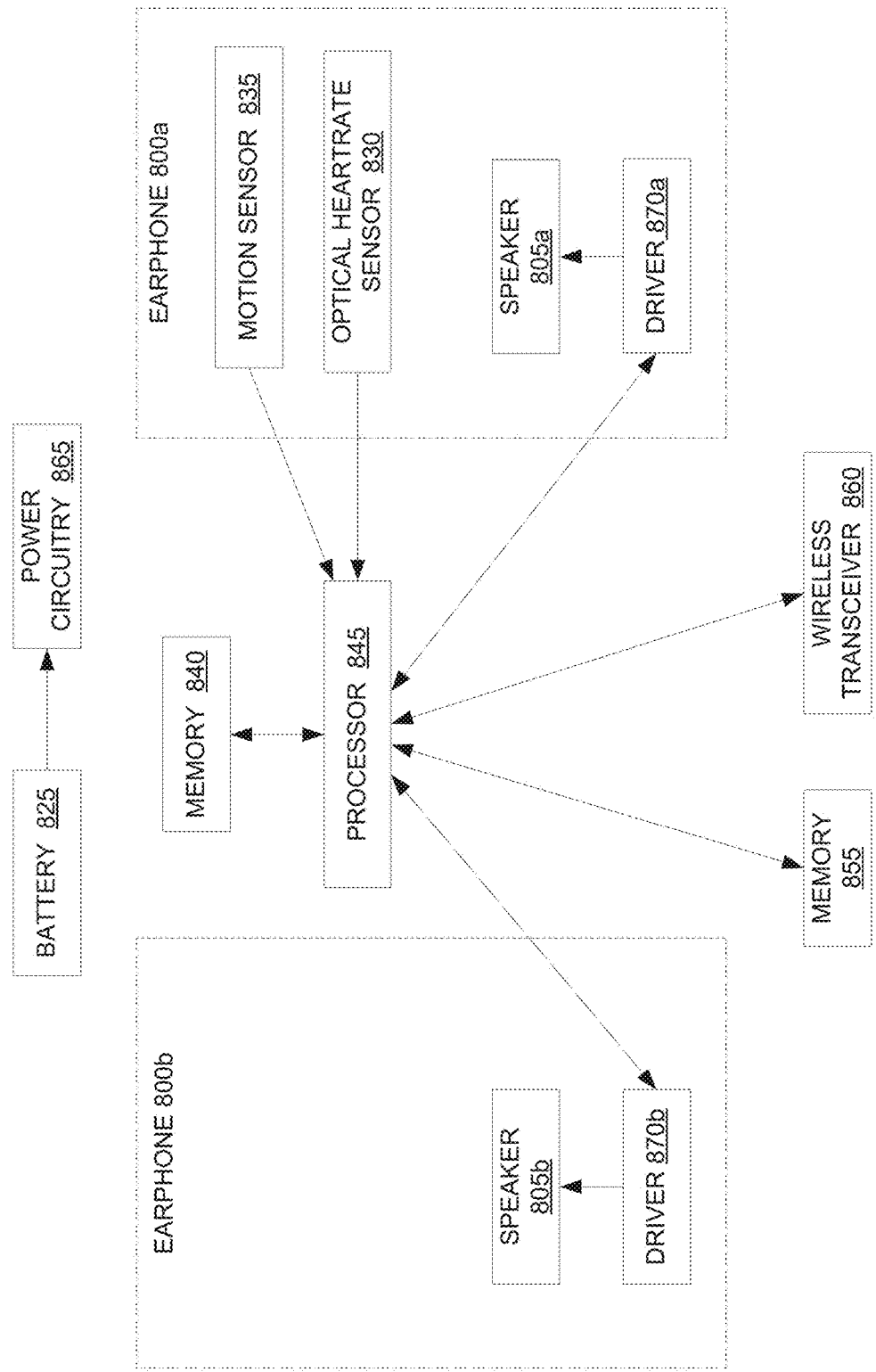
FIG. 8B illustrates an example architecture for circuitry of earphones, in accordance with various embodiments.

With reference to FIG. 8B, the circuitry of earphones 800 may include processor 845 (including, in some instances, logic circuits similar to logic circuits 340), memories 840, 855, wireless transceiver 860, battery 825, power circuitry 865, and other circuitry for earphones 802a, 802b. As further illustrated earphone 802a may include motion sensor 835, optical heartrate sensor 830, speaker 805a, and driver 870a. Earphone 802b may include any of these components, and in the illustrated embodiment includes speaker 805b and driver 870b. In additional embodiments, earphone 802b may also include a motion sensor (e.g., an accelerometer or gyroscope, generally, similar to motion sensor 835), and/or an optical heartrate sensor (e.g., optical heartrate sensor 830). Motion sensor 835, including any subcomponents thereof (e.g., as described above), and/or optical heartrate sensor 830 may be included entirely within a single earphone (e.g., earphone 802a), may be distributed between two earphones 802a, 802b, or may be duplicated within each earphone 802a, 802b in any combination for added precision, such that each earphone 802a, 802b in the pair can detect and activity and biometrics information as desired for particular applications.

Processor 845 may include logic circuits for receiving, processing, and/or storing information gathered by bio sensors (e.g., optical heartrate sensor 830) and/or motion sensor 835. More particularly, as illustrated in FIG. 8B, processor 845 may be coupled (e.g., by wired or wireless connection) to motion sensor 835 and optical heartrate sensor 830, and hence may receive and process electrical signals generated by these sensors 835 and/or 830 in response to the wearer's motion and biometrics, respectively. Processor 845 may store such signals or processed versions thereof as biometric data and/or activity data in memory 840, which biometric data and/or activity data may be made available to a computing device 1215 using wireless transceiver 860. In some embodiments, memory 840 stores biometric data and/or activity data for transmission by wireless transceiver 860 to computing device 1215 for further processing thereby.

During operation, optical heartrate sensor 830 may use a photoplethysmogram (PPG) to optically obtain the user's heart rate. In one embodiment, optical heartrate sensor 830 includes a pulse oximeter that detects blood oxygenation level changes as changes in coloration at the surface of a user's skin. More particularly, in this embodiment, optical heartrate sensor 830 illuminates the skin of the user's ear using a light-emitting diode (LED). Light from the LED penetrates through the epidermal layers of the skin to underlying blood vessels. A portion of the light is absorbed, while a portion of the light is reflected back to optical heartrate sensor 830. The light reflected back through the skin of the user's ear is then obtained with a receiver (e.g., a photodiode) and used to detect changes in the user's blood oxygen saturation ($SpO_2$) and pulse rate, thereby permitting calculation of the user's heart rate using algorithms known in the art (e.g., using processor 840). Optical heartrate sensor 830 may be positioned on one of earphones 802a, 802b such that optical heartrate sensor 830 is proximal to the interior side of a user's tragus when earphones 800 are worn. In other embodiments, optical heartrate sensor 830 may be positioned on one of earphones 802a, 802b so as to be proximal to any other portion of the user's ear (e.g. concha, ear lobe, pinna, antitragus, outer ear canal, etc.) when earphone 802a, 802b is worn by the user.

In this manner, optical heartrate sensor 830 may also be used to generate biometrics that may be used calculate or estimate the wearer's heart rate variability (HRV), i.e. the variation in time interval between consecutive heartbeats. For example, processor 845 or a processor resident in computing device 1215 may calculate HRV using the biometrics gathered by optical heartrate sensor 830 based on a time domain methods, frequency domain methods, and/or other methods known in the art that estimate/calculate HRV based on data such as mean heart rate, change in pulse rate over a time interval, and other data used in the art to estimate/calculate HRV. These methods of calculating HRV may also be applied with respect to biometrics gathered using band 100.

In further embodiments, logic circuits of processor 845 may further detect, calculate, and/or store activity data, based on measured activity of the wearer, such as the wearer's amount of physical activity (e.g., exercise and the like), sleep, or rest over a period of time, or the amount of time without physical activity over a period of time. The logic circuits may use the HRV, the activity data, or some combination of the two to gauge the wearer's response to the activity and other external factors (e.g., temperature, weather, stress, etc.). In various embodiments, the user's response may indicate the user's physical condition and aptitude for further physical activity for the current or next day, as will be described in further detail herein.

Referring again to FIG. 8B, during audio playback, earphones 800 may wirelessly receive audio data using wireless transceiver 860. The audio data may then be processed by logic circuits of processor 845, for example, to be converted into electrical signals and delivered to respective drivers 870a, 870b of speakers 805a, 805b, such that the electrical signals may be converted to sound. Drivers 870a, 870b may use various driver technologies known in the art, for example, moving coil drivers, electrostatic drivers, electret drivers, orthodynamic drivers, and other transducer technologies may be used.

Wireless transceiver 860 may be configured to transmit/receive biometrics, activity, and audio data across link 1280 and 1290, for example using available wireless communications protocols/standards or methods. In some embodiments, wireless transceiver 860 may utilize BLUETOOTH, ZIGBEE, Wi-Fi, GPS, cellular technology, or some combination thereof. Further, although FIG. 8B illustrates a single wireless transceiver 860 for transmitting/receiving biometrics, activity, and audio data, in an alternative embodiment, separate transceivers may be dedicated for communicating biometric data to/from computing device 1215, for communicating activity data to/from computing device 1215, and for communicating audio data to/from computing device 1215. In some cases, transceiver 860 may include a low energy transmitter such as a near field communications (NFC) transmitter or a BLUETOOTH low energy (LE) transmitter. In further example implementations, a separate wireless receiver may be provided for receiving high fidelity audio data from an audio source. In yet additional embodiments, a wired interface (e.g., micro-USB) may be used for communicating data stored in memories 840 and/or 855.

FIG. 8B also shows that earphones 800 may be powered by battery 825, which may be coupled to power circuitry 865. Any suitable battery or power supply technologies known in the art may be used. For example, a lithium-ion battery, aluminum-ion battery, piezo or vibration energy harvesters, photovoltaic cells, or other like devices may be used. In some deployments of earphones 800, battery 825 may be enclosed in earphone 802a or 802b. Alternatively, battery 825 may be enclosed in controller 820. The circuitry of headphones 800 described herein may be configured to enter a low-power or inactive mode when earphones 800 are not in use, or in other scenarios where low-power operation is appropriate. For example, mechanisms such as an on/off switch, a BLUETOOTH transmission disabling command, or the like may be provided by controller 820, such that a user may manually control the on/off state of one or more power-consuming components or circuits of earphones 800.

It should be noted that in various embodiments, processor 845, memories 840 and 855, wireless transceiver 860, battery 825, and power circuitry 865 may be enclosed in and/or distributed throughout either or both of earphone 802a, earphone 802b, and controller 820. For example, processor 845 and memory 840 may be enclosed in earphone 802a along with optical heartrate sensor 830 and motion sensor 835. In this particular scenario, these components may be electrically coupled to a printed circuit board (PCB) enclosed in earphone 802a. Additionally, any one or more of these components may be duplicated in each of earphones 802a, 802b.

Figure 9C:
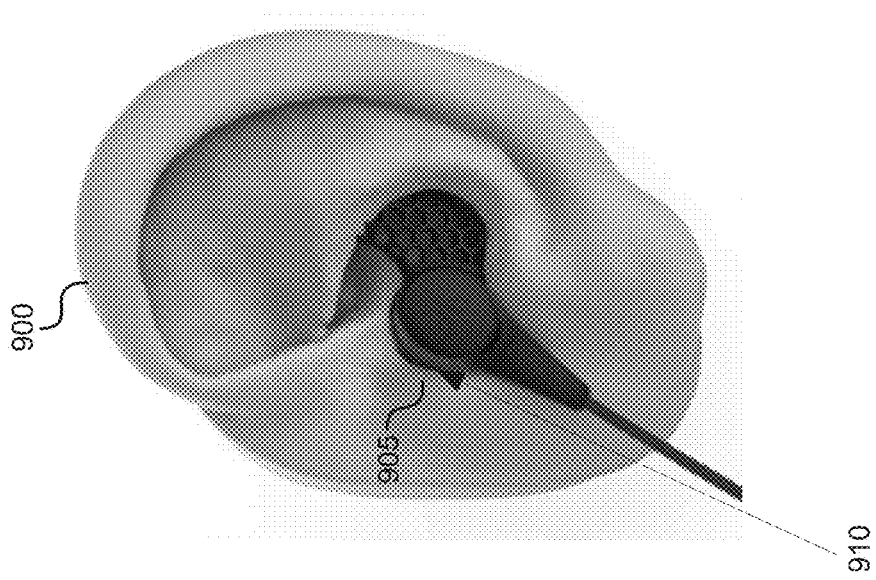
FIG. 9C illustrates a frontal perspective view of embodiments of an example earphone placed in a user's ear, in accordance with the present disclosure.
Figure 9B:
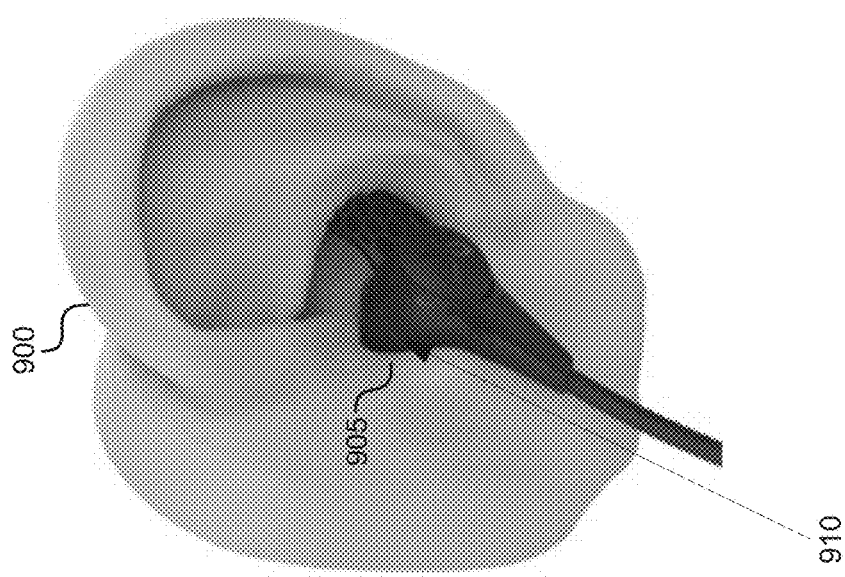
FIG. 9B illustrates a side view of embodiments of an example earphone placed in a user's ear, in accordance with the present disclosure.
Figure 9A:
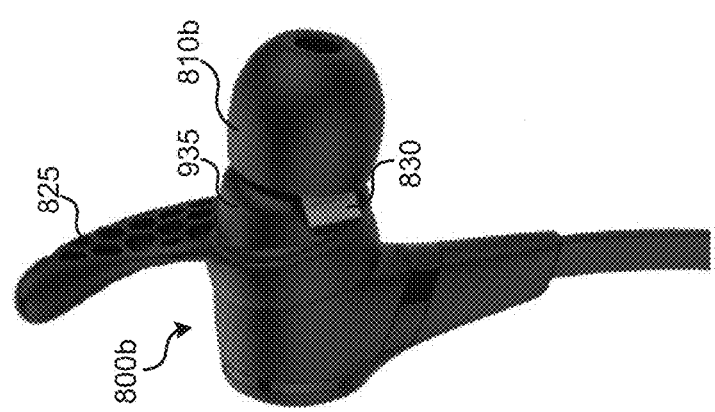
FIG. 9A illustrates a perspective view of embodiments of an example earphone placed in a user's ear, in accordance with various embodiments.

FIG. 9A illustrates a perspective view of embodiments of earphone 802b. As shown, earphone 802b may include optical heartrate sensor 830, as generally described above. FIG. 9A will be described in conjunction with FIGS. 9B and 9C, which show various perspective views illustrating example arrangements of optical heartrate sensor 830 when earphone 802b (or 802a) is worn in a user's ear 900. As shown, earphone 802b may include body 935, tip 810b, fin 825, and optical heartrate sensor 830. Optical heartrate sensor 830 protrudes from a frontal side of body 935, proximal to tip 810b, and proximal to a nozzle (not shown) of earphone 802b. FIGS. 9B and 9C illustrate interface 910 of optical heartrate sensor 830 and ear 900 when earphone 802b is worn in a user's ear 900. In the illustrated embodiments, when earphone 802b is worn, optical heartrate sensor 830 is proximal to the interior side of the user's tragus 905. In various embodiments, earphones 802a, 802b may be dual-fit earphones shaped to be comfortably and securely worn in either an over-the-ear configuration or an under-the-ear configuration. The secure fit provided in such embodiments aids in keeping optical heartrate sensor 830 positioning on the interior side of tragus 860, thereby ensuring accurate and consistent measurements of a user's heartrate information.

Figure 9F:
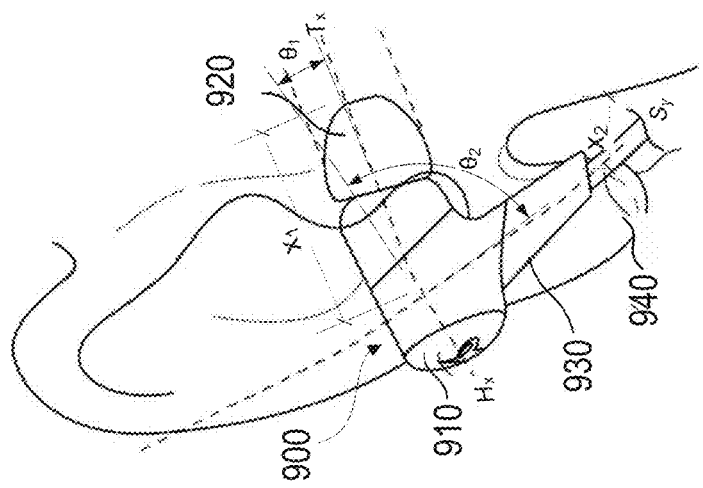
FIG. 9F illustrates a cross-sectional view of an example earphone, in accordance with various embodiments.
Figure 9E:
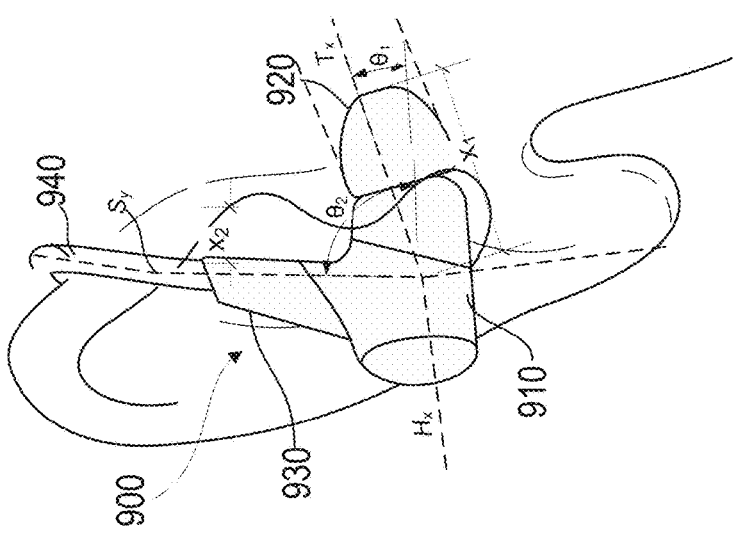
FIG. 9E illustrates a cross-sectional view of an example earphone, in accordance with various embodiments.
Figure 9D:
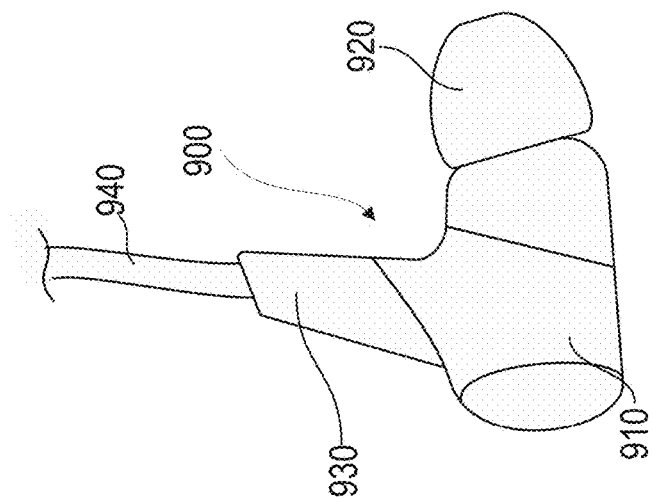
FIG. 9D illustrates a cross-sectional view of an example earphone, in accordance with various embodiments.

FIGS. 9D and 9E illustrate earphones 950 in an over-the-ear configuration, whereas FIG. 9F illustrates earphones 950 in an under-the-ear configuration. As illustrated, earphone 950 includes housing 910, tip 920, strain relief 930, and cable 940. The proximal end of tip 920 mechanically couples to the distal end of housing 910. Similarly, the distal end of strain relief 930 mechanically couples to a side (e.g., the top side) of housing 910. Furthermore, the distal end of cord 940 may be disposed within and secured by the proximal end of strain relief 930.

Referring to FIGS. 9E and 9F, the longitudinal axis of housing 910, $H_x$, forms angle $\theta_1$ with respect to the longitudinal axis of tip 920, $T_x$. The longitudinal axis of strain relief 930, $S_y$, may align with the proximal end of strain relief 930 and form angle $\theta_2$ with respect to the axis $H_x$. In some embodiments, $\theta_1$ is greater than 0 degrees, e.g., $T_x$ extends in at an angle from $H_x$, or in other words, tip 920 may be angled with respect to housing 910. The value of $\theta_1$ may be selected to approximate the ear canal angle of the wearer. For example, $\theta_1$ may range between 5 degrees and 15 degrees, and may extend from 0 degrees 45 degrees. Also, $\theta_2$ may be less than 90 degrees, e.g., such that $S_y$ extends at a non-orthogonal angle from $H_x$, or in other words, strain relief 930 is angled with respect to a perpendicular orientation with housing 910. In some embodiments, $\theta_2$ may be selected to direct the distal end of cable 940 closer to the wearer's ear. For example, $\theta_2$ may range between 75 degrees and 89 degrees, but may extend to as low as 45 degrees in some situations.

As further illustrated in FIGS. 9E and 9F, $x_1$ may represent the distance between the distal end of tip 920, on the one hand, and the intersection of strain relief 930's longitudinal axis $S_y$ and housing longitudinal axis $H_x$, on the other hand. One of skill in the art would, upon studying the present disclosure, appreciate that the dimension $x_1$ may be selected based on several parameters, including, for example, the desired fit to a wearer's ear based on the average human ear anatomical dimensions, the types and dimensions of electronic components (e.g., optical heartrate sensor 830, motion sensor 835, processor 845, memories 840 and 855, other components described in this connection, and so on) that may be disposed within housing 910 and tip 920, and based on the specific placement of optical heartrate sensor 830. In some examples, $x_1$ may be at least 18 mm. However, in other examples, $x_1$ may be smaller or greater based on the parameters discussed above.

Referring again to FIGS. 9E and 9F, $x_2$ may represent the distance between the proximal end of strain relief 930 and the surface of the wearer's ear. In the illustrated configurations, $\theta_2$ may be selected to reduce $x_2$, as well as to direct cable 940 toward the wearer's ear, such that cable 940 may rest in the crevice formed where the top of the wearer's ear meets the side of the wearer's head. In some embodiments, $\theta_2$ may range between 75 degrees and 89 degrees, but may extend to as low as 45 degrees in some situations.

In some examples, strain relief 930 may be made of a flexible material such as rubber, silicone, or soft plastic, so as to enable strain relief 930 to be bent toward the wearer's ear. Similarly, strain relief 930 may include a shape memory material so as to retain the shape thereof after being bent inward. In some examples, strain relief 930 may be shaped to curve inward towards the wearer's ear.

As one having skill in the art would appreciate from the above description, earphones 800 and band 100 may in various embodiments gather biometric data and activity data that may be used to track a user's activities and activity level. The biometric data and activity data may then be made available to computing device 1215, which may provide a GUI for interacting with the data using a tracking application installed on computing device 1215. FIG. 10A is a block diagram illustrating example components of computing device 1215, including an installed tracking application (occasionally referred to as an app) 1015.

With continued reference to FIG. 10A, computing device 1215 may include connectivity interface 1005, storage 1010 that stores activity tracking application 1015, processor 1020, graphical user interface (GUI) 1025 that may be provided on display 1030, and bus 1035 for transferring data between the various components of computing device 1215. Connectivity interface 1005 connects computing device 1215 to earphones 800 and/or band 100 through a communication medium (e.g., links 1280 and 1290). Storage 1010 may include volatile memory (e.g. RAM), non-volatile memory (e.g. flash storage), or some combination/variation thereof. In various embodiments, storage 1010 may store biometric data and/or activity data collected by earphones 800 and/or band 100. Additionally, storage 1010 may store tracking application 1015 that, when executed by processor 1020, receives input (e.g., by a conventional hard/soft key or a touch screen, voice detection, or other input mechanism), and allows a user to interact with the collected biometric and/or activity data.

In various embodiments, a user may interact with tracking application 1015 via GUI 1025, which may be provided by display 1030, for example, a touchscreen display that accepts various hand gestures as inputs. Tracking application 1015 may process the biometric and/or activity data collected by earphones 800 and/or band 100, and present the data via display 1030. Before describing tracking application 1015 in further detail, it should be noted that in some embodiments earphones 800 and band 100 may filter the collected biometric and activity data prior to transmitting the same to computing device 1215. Accordingly, although the embodiments disclosed herein are described with reference to tracking application 1015 processing the received data, in various implementations, preprocessing operations, and/or any one or more of the other processing operations disclosed herein, may be performed by processor 845 of earphones 800, or by logic circuits 340, prior to transmission of the data to computing device 1215.

Tracking application 1015 may be initially configured/setup (e.g., after installation on a smartphone or other computing device 1215) based on a user's self-reported biological information, sleep information, and activity preference information. For example, during setup, the user may be prompted via display 1030 to enter biological information such as the user's gender, height, age, weight, etc. Further, during setup the user may be prompted for sleep information, such as the amount of sleep needed by the user and the user's regular bed/wake time. Further still, the user may be prompted during setup for a preferred activity level and/or intensity, as well as types of activities the user desires to be tracked (e.g., running, walking, swimming, dancing, biking, hiking, etc.) In various embodiments of the disclosure, this self-reported information may be used in tandem with the information collected by earphones 800 and/or band 100.

Following the setup, tracking application 1015 may be used by a user to monitor activity and biometrics of the user (e.g., based on sensors 835 and 830). As further illustrated in FIG. 10B, tracking application 1015 may include various modules, such as, for example, display module 1050, bio sensor module 1055, performance profile module 1060, and motion sensor module 1065. These modules may be implemented separately or in combination. Each module may include computer-readable media and have computer-executable code stored thereon, such that the code may be executed by processor module 1020 (e.g., in some cases in conjunction with processing modules 1070) to perform specific functions (e.g., as described herein with regard to various flow charts etc.) with respect to biometric and/or activity data available to tracking application 1015. As will be further described below, display module 1050 may present (e.g., via display 1030) various screens to a user, with the screens containing graphical representations of information provided by tracking app 1015. In further embodiments, tracking application 1015 may be used to display to the user an instruction for wearing and/or adjusting earphones 800.

FIG. 11 is an operational flow diagram illustrating example method 1100 that provides an earphone adjustment feedback loop to increase the likelihood of accurate biometric data collection by earphones 800. At operation 1110, tracking application 1015 may be executed, which may in turn result in displaying an instruction to the user on how to wear earphones 800 to obtain an accurate and reliable signal from optical heartrate sensor 830 and/or motion sensor 835. Operation 1110 may occur only once, upon installation of tracking application 1015, may occur once per day (e.g., when the user first wears earphones 800 in the day), or at any customizable, programmable, and/or predetermined interval.

Operation 1120 involves providing feedback (e.g., by a display such as display 1030 on computing device 1215) to the user regarding the quality of the signal received from one or both of optical heartrate sensor 830 and/or motion sensor 835, based on the positioning of earphones 1100. For example, a signal quality bar or other graphical elements may be displayed to the user. Alternatively, an audio signal may be used to provide the feedback.

At decision 1130, it is determined if the biosensor signal quality is satisfactory for accurate biometric and activity data to be gathered/used. In various embodiments, this determination may be based on factors such as, for example, the frequency with which optical heartrate sensor 830 is collecting heart rate data and/or with which motion sensor 835 is collecting activity information, the variance in the measurements of optical heartrate sensor 830 and/or activity information (including location-based information), dropouts in heart rate measurements by sensor 830, the signal-to-noise ratio approximation of optical heartrate sensor 830 and/or motion sensor 835, the amplitude of the signals generated by sensors 835 and/or 830, and the like.

If the signal quality is determined (e.g., at operation 1130) to be unsatisfactory, at operation 1040, tracking application 1015 may display instructions for adjusting earphones 800 to improve the signal, and operations 1120 and decision 1130 may subsequently be repeated. For example, instruction on adjusting strain relief 930 of earphone 950 may be displayed. Otherwise, if the signal quality is satisfactory, at operation 1150, application 1015 may display confirmation of good signal quality and/or good position of earphones 800. Subsequently, tracking application 1015 may proceed with normal operation.

Figure 12A:
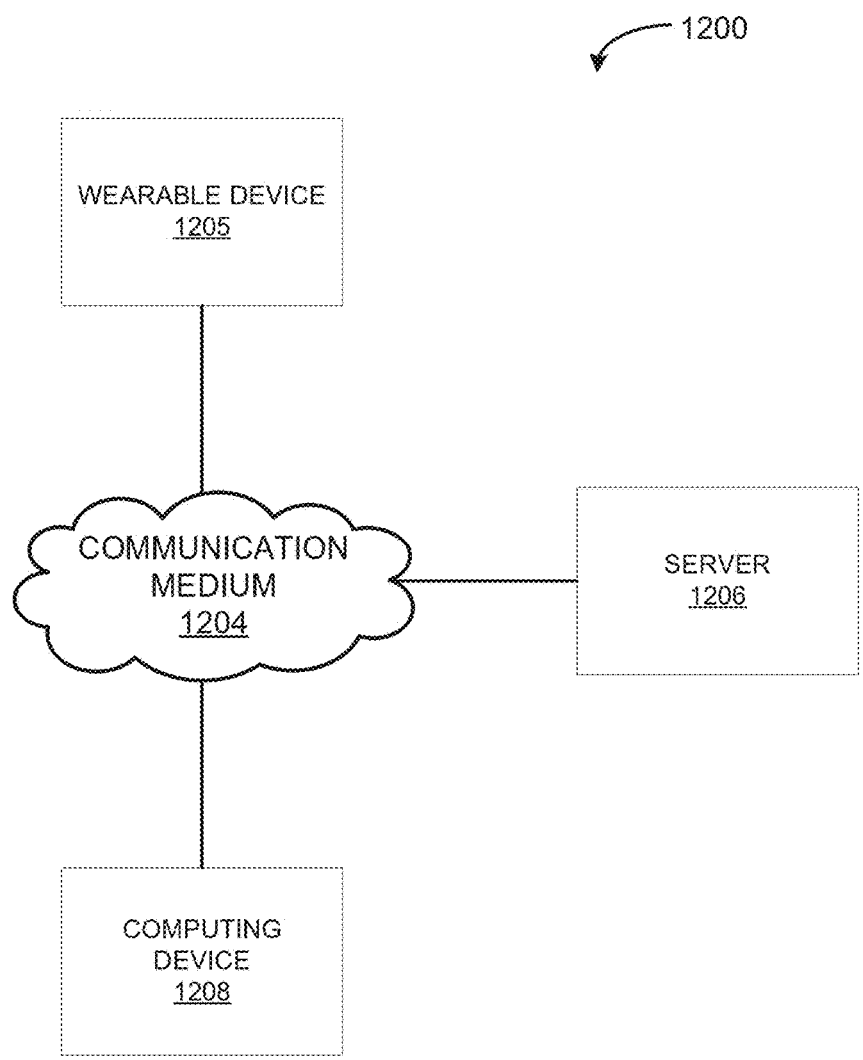
FIG. 12A is an example system in which various embodiments of the disclosure may be implemented.

FIG. 12A illustrates example system 1200 in which various embodiments of the disclosure may be implemented. By way of example, system 1200 may be used to determine performance capacity of a user. System 1200 includes wearable device 1202, communication medium 1204, server 1206, and computing device 1208. Embodiments of system 1200 are capable of capturing and tracking robust information related to a user's activity, including information about the user's activity type, duration, intensity, and so on. Moreover, embodiments of system 1200 are also capable of tracking and capturing and tracking robust information related to a user's biometrics. This wealth of information, which may be gathered by various sensors as described herein, may be used to provide a user-specific response profile that is based on biometric and/or activity data. Being user-specific, the response profile provided by system 1200 may be personalized and accurate. Further, in some embodiments, a model may be created based on the gathered activity/biometric data, such that the response profile may be used to predict the user's response to various training loads. An accurate and personalized response profile of this nature may allow the user to make informed decisions regarding the user's training load and/or lifestyle, thus achieving maximum performance and balance.

Referring again to FIG. 12A, wearable device 1202 may include in some embodiments, band 100 or headphones 800. Communication medium 1204 may be used to connect or communicatively couple wearable device 1202, server 1206, and/or computing device 1208 to one another or to a network, and communication medium 1204 may be implemented in a variety of forms. For example, communication medium 1204 may include an Internet connection, such as a local area network (LAN), a wide area network (WAN), a fiber optic network, internet over power lines, a hard-wired connection (e.g., a bus), and the like, or any other kind of network connection. Communication medium 1204 may be implemented using any combination of routers, cables, modems, switches, fiber optics, wires, radio (e.g., microwave/RF links), and the like. Further, communication medium 1204 may be implemented using various wireless standards, such as Bluetooth®, Wi-Fi, 3GPP standards (e.g., 2G GSM/GPRS/EDGE, 3G UMTS, or 4G LTE), etc. Upon reading the present disclosure, one of skill in the art will recognize other ways to implement communication medium 1204 for communications purposes.

Server 1206 generally directs communications made over communication medium 1204. Server 1206 may include, for example, an Internet server, a router, a desktop or laptop computer, a smartphone, a tablet, a processor, a module, or the like, and may be implemented in various forms, include, for example, an integrated circuit, a printed circuit board, or in a discrete housing/package. In one embodiment, server 1206 directs communications between communication medium 1204 and computing device 1208. For example, server 1206 may update information stored on computing device 1208, or server 1206 may send/receive information to/from computing device 1208 in real time. Server 1206 may also be used to implement cloud computing capabilities for wearable device 1202 and/or computing device 1208.

Computing device 1208 may take a variety of forms, such as a desktop or laptop computer, a smartphone, a tablet, a smartwatch or other wearable electronic device, a processor, a module, earphones, or the like. By way of illustration, computing device 1208 may include a processor or module embedded in a wearable sensor, a bracelet, a smart-watch, a piece of clothing, an accessory, and so on. Computing device 1208 may be, for example, substantially similar to devices embedded in electronic capsule 200, which may be embedded in and/or removable from band 100, as illustrated in FIGS. 2 through 7 and described herein. Computing device 1208 may communicate with other devices over communication medium 1204 with or without the use of server 1206. In one embodiment, wearable device 1202 includes computing device 1208. Further, computing device 1208 may in some cases be computing device 1215 or be substantially similar thereto, and in this regard, the description of computing device 1215 herein may apply equally to computing device 1208, and vice versa. In various embodiments, wearable device 1202 or computing device 1208 may be used to perform various processes described herein and/or may be used to execute various operations described herein with regard to one or more disclosed systems and methods. Upon studying the present disclosure, one of skill in the art will appreciate that system 1200 may include multiple wearable devices 1202, communication media 1204, servers 1206, and/or computing devices 1208.

Figure 12B:
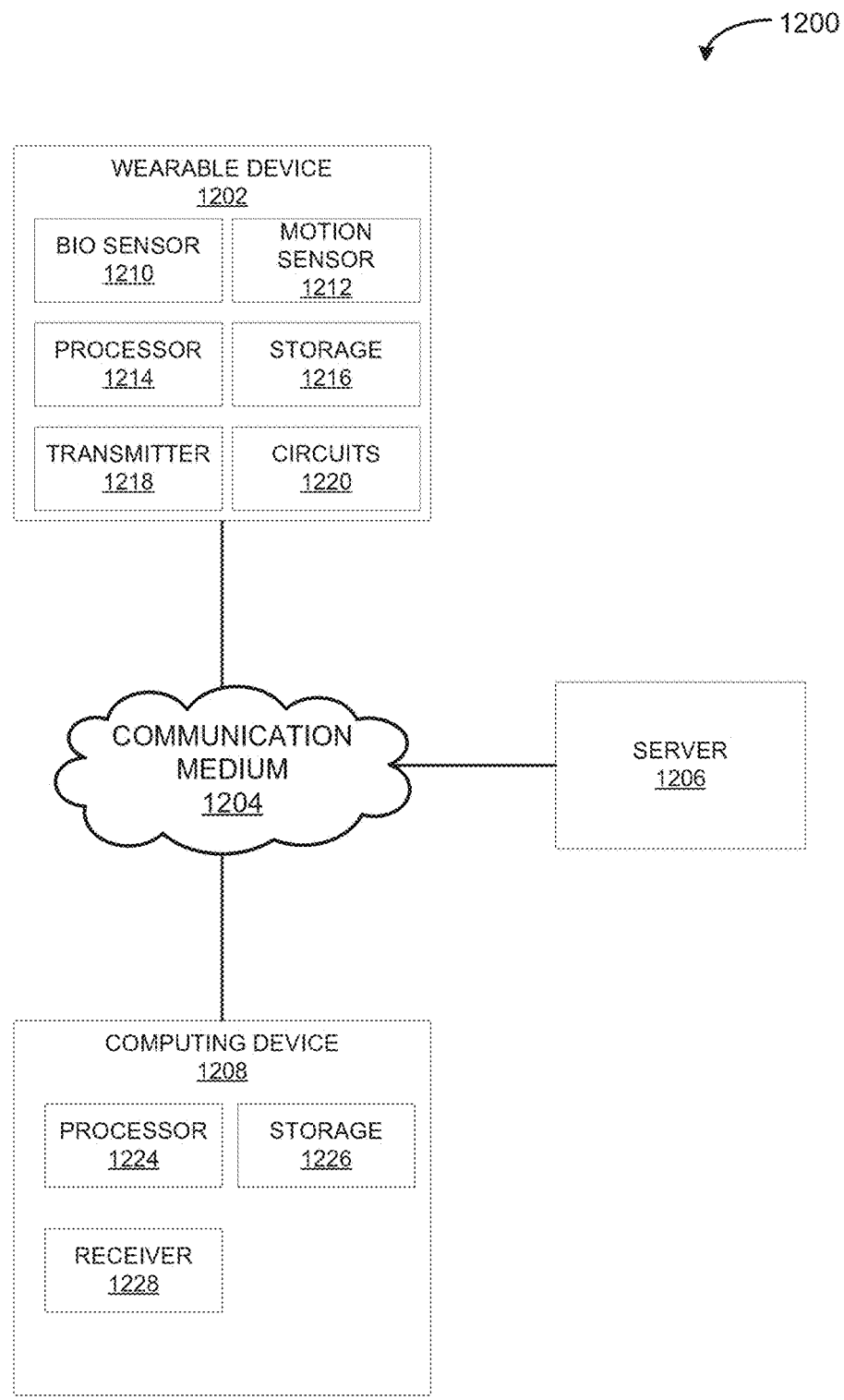
FIG. 12B is an example system in which various embodiments of the disclosure may be implemented.

FIG. 12B illustrates one embodiment of system 1200, and specifically, provides further detail of some example implementations of wearable device 1202 and computing device 1208, in accordance with the present disclosure. In the embodiments of FIG. 12B, wearable device 1202 includes bio sensor 1210 and motion sensor 1212. In one specific example, wearable device 1202 further includes processor 1214. Processor 1214 may be coupled to bio sensor 1210 and motion sensor 1212, and may be configured to process electrical signals generated by bio sensor 1210 and/or motion sensor 1212. Such signals may be indicative of biometrics and activity, as will is described in further detail herein. Bio sensor 1210 may be implemented as any of the various sensors described herein for measuring biometrics of a user—e.g., with respect to FIGS. 1 through 11. In this connection, bio sensor 1210 may include one or more sensors, e.g., finger bio sensor 220, wrist bio sensor 210, and optical heartrate sensor 830. Likewise, motion sensor 1212 may be implemented as any of the various motion sensors described herein for detecting motion (e.g., by way of various inertial units), as described, e.g., with reference to FIGS. 1 through 11.

Furthermore, wearable device 1202 may include circuits 1220 that receive and process the electrical signals from bio sensor 1210 and motion sensor 1212. For example, circuits 1220 may include an analog-to-digital converter, an encoder, modem circuitry, and the like, that receive electrical signals from bio sensor 1210 and motion sensor 1212 and process the electrical signals into a format that may be acceptable to processor 1214 or that may be transmitted over communication medium 1204 by transmitter 1218. Storage 1216 may also be included in embodiments of wearable device 1202, and may be used to store activity data and/or biometric data generated from the electrical signals output by bio sensor 1210 and/or motion sensor 1212. This stored data may then be processed by processor 1214 and used locally to wearable device 1202, or be transmitted by transmitter 1218. Additionally, storage 1216 and 1226 may include non-transitory computer-readable media having instructions stored thereon that, when executed, cause processor 1214 and/or 1224 to perform various functions, including, by way of example, any of the operations described with reference to methods 1300 and 1400 (and FIGS. 13 and 14) and elsewhere herein, and to make various calculations, or control or communicate with any of the other various other hardware components described herein.

As further depicted in FIG. 12B, system 1200 for determining performance capacity also includes receiver 1228. Receiver 1228 may be part of and/or embedded within computing device 1208 (e.g., may be implement at least in part as an integrated circuit). Receiver 1228 may be a wireless receiver, and receiver 1228 receives biometric data and activity data. For example, receiver 1228 may receive the biometric and activity data over communications medium 1204 from transmitter 1218. The biometric data may be indicative of biometrics measured by bio sensor 1210 in wearable device 1202, and the activity data may be indicative of activity data monitored by motion sensor 1212.

Figure 13:
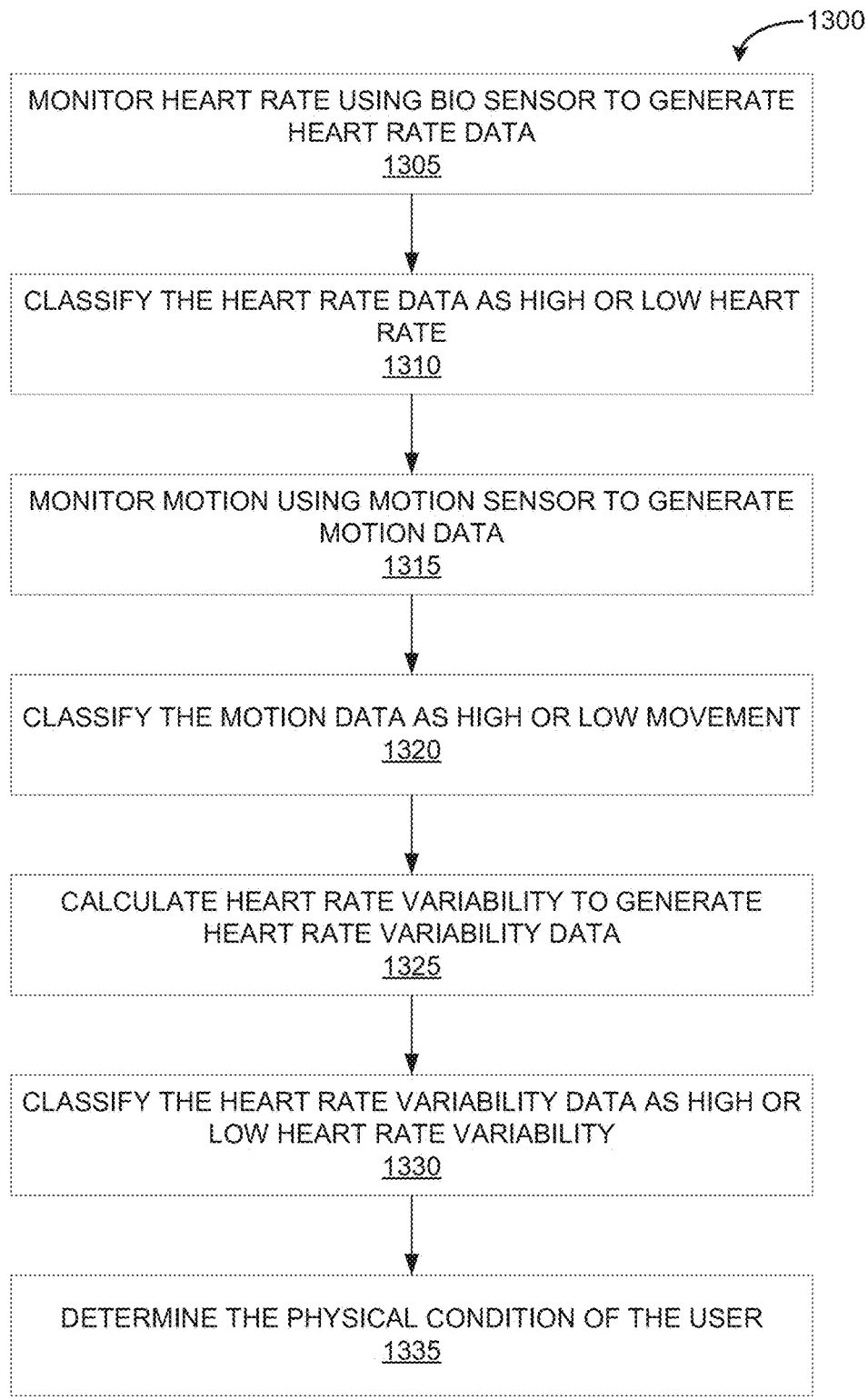
FIG. 13 is an example operational flow diagram illustrating various operations that may be performed to provide the current physical condition of the user, in accordance with various embodiments described herein.

FIG. 13 is an example operational flow diagram illustrating various operations that may be performed to provide the current physical condition of the user, in accordance with various embodiments described herein. The operations and sub-operations of method 1300 may be carried out, in some cases, by one or more of the components/elements/devices/modules of communication environment 1600, computing device 1215, tracking application 1015, and system 1200, described above and referenced in FIGS. 1, 8A, 8B, 9A-9F, 10A, 10B, 12A and 12B, as well as sub-components/elements/devices/modules depicted therein or described with respect thereto. In such instances, the description of method 1300 may refer to the corresponding component/element, but in any case, one of skill in the art will recognize when the corresponding component/element may be used, whether or not there is explicit reference thereto. Furthermore, it will be appreciated that such references do not necessarily limit method 1300 to the particular component/element referred to. Thus, it will be appreciated by one of skill in the art that aspects and features described above in connection with (sub-) components/elements/devices/modules, including variations thereof, may be applied to the various operations described in connection with method 1300. Generally, method 1300 facilitates generating and providing a user his or her current physical condition based on the gathered biometric data (heart rate, HRV) and monitored motion data (movement associated with physical exercise, rest, sleep, etc.).

Referring now to FIG. 13, at operation 1305 of method 1300, the heart rate is monitored using the bio sensor (e.g., bio sensor 1210) to gather and store the user's heart rate associated with the activities performed throughout the day. The bio sensor may further include optical sensors such as a heart rate sensor or oximeter to generate the heart rate data. The heart rate data may be continuously generated and stored throughout the day and night as long as the bio sensor (band 100) is continuously worn by the user. In other instances, the bio sensor may collect the user's heart rate data in pre-determined established time intervals (e.g., every 30 seconds, every 5 minutes, every 1 hours, every 3 hours, etc.) all throughout the day as long as the bio sensor (band 100) is continuously worn by user. In some embodiments, the heart rate data may also be gathered and collected by earphones 800 at pre-determined established time intervals as long as the earphones are worn by the user.

Gathering and generating heart data may involve circuits 1220 by converting electrical signals from the bio sensor 1201 to a format that a processor 1214 may process, store in storage 1216, and/or transmit by transmitter 1218. For example, the biometric data may be generated from biometrics through analog-to-digital conversion, filtering of the heart rate data, and/or encoding of the biometrics or data indicative thereof. Additionally, operation 1310 may also be performed by a processor 1214 or 1224. For example, storage 1216 or 1226 may include a non-transitory computer readable medium operatively coupled to processor 1214 or 1224 and storing instructions thereon that, when executed, cause processor 1214 or 1224 to generate heart rate data from the heart rate monitored by the bio sensor 1210, including using circuits 1220.

At operation 1310 of method 1300, the generated and stored heart rate data is then analyzed to categorize the heart rate data as high or low heart rate relative to the user's maximum heart rate. The user's maximum heart rate may be determined by incorporating individual factors of each user, such as age, gender, and weight. Additionally, the user's maximum heart rate may be input manually by the user.

The categorization of the user's heart rate data as high or low heart rate may be determined by characterizing the heart rate data into one second data samples for analysis. Additionally, the heart rate data samples may be collected and analyzed to at select time intervals (e.g., every 1 minute, 5 minute, 10 minute, 1 hours, 2 hours, etc.) throughout the day. In the instance that the pre-determined number of heart rate data samples for a select time interval consists of heart rate data samples that are at least 50% of the user's maximum heart rate, the heart rate data may be categorized as high heart rate. In other instances, a low heart rate may be established when a pre-determined number of heart rate data samples for a select time interval consists of heart rate data samples that are less than 50% of the user's maximum heart rate. As an example, if more than 150 samples within an established 5 minute interval period for heart rate assessment is less than 50% of the user's maximum heart rate, that particular time interval may be classified as the user having a low heart rate. As an additional example, if more than 150 samples within an established 5 minute interval period for heart rate assessment is more than 50% of the user's maximum heart rate, that particular time interval may be classified as the user having a high heart rate. The heart rate data corresponding to each select time interval may be continuously gathered and stored so that the user's aggregated heart rate data may be used to determine the physical condition of the user (described in greater detail below).

At operation 1315 of method 1300, the user's motion may be monitored using a motion sensor (e.g., motion sensor 1212) embedded in the wearable device (e.g., wearable device 1202) to generate motion data. The motion sensor 1212 may include an accelerometer to measure acceleration associated with change in the user's movement. Monitoring a user's motion may include determining the activity associated with the user's movement (e.g., sleeping, running, biking, swimming, cycling, etc.). Additionally, the motion sensor may generate motion data by converting a user's motion into electrical signals.

At operation 1320 of method 1300, the electrical signals generated from the user's motion may be collectively stored and analyzed to categorize the motion data as high or low movement at select time intervals (e.g., every 1 minute, 5 minute, 10 minute, 1 hours, 2 hours, etc.), otherwise known as an EPOCH. As such, at the end of each EPOCH or select number of EPOCHs, the motion data may be categorized as high or low movement. By way of example only, in the instance that the motion sensor detects the user's motion as sleep or inactive motion for 15 or more consecutive EPOCHs, the motion data may be categorized as low movement for that particular time interval. In contrast, if the motion sensor detects the user's motion as active motion (e.g., walking, running, swimming, cycling, etc.) for 15 or more consecutive EPOCHs, the motion data may be categorized as high movement for that particular time interval. However, it should be noted that classifying the user's motion as high or low movement need not be determined within 15 consecutive EPOCH periods, and instead, may be determined within any specified time intervals as selected. The motion data corresponding to each EPOCH time interval may be continuously gathered and stored so that the motion data may be used to determine the physical condition of the user (described in greater detail below).

At operation 1325, method 1300 includes calculating HRV from the biometrics measured by the bio sensor. The HRV may be calculated and stored continuously throughout the day. In other instances, the HRV may be calculated and stored in pre-determined established intervals (e.g., every 30 seconds, every 5 minutes, every 1 hours, every 3 hours, etc.). This may involve circuits 1220 converting electrical signals from the bio sensor 1201 to a format that a processor 1214 may process, store in storage 1216, and/or transmit by transmitter 1218. For example, the HRV data may be generated from biometrics through analog-to-digital conversion, filtering of the HRV data, and/or encoding of the biometrics or data indicative thereof. Additionally, operation 1310 may also be performed by a processor 1214 or 1224. For example, storage 1216 or 1226 may include a non-transitory computer readable medium operatively coupled to processor 1214 or 1224 and storing instructions thereon that, when executed, cause processor 1214 or 1224 to generate heart rate data from the heart rate monitored the bio sensor 1210, including using circuits 1220.

At operation 1330 of method 1300, the generated HRV data may be further categorized as high or low HRV. In one particular embodiment, the categorization of a user's HRV as high or low may be determined with respect to each low movement and high movement period generated from the motion data (operation 1320). The mean and standard deviation of the HRV data with respect to each low/high movement may be calculated to determine the statistical standard score, or Z score. In the particular instance that the Z score for each high/low movement period is less than a determined Z score value, the HRV data may be categorized as low HRV. In the instance that the Z score for each high/low movement period is greater than a determined Z score value, the HRV data may be categorized as high HRV. By way of example only, a calculated Z score that is less than 0.67 may be categorized as low HRV. By way of another example only, a calculated Z score that is greater than 0.67 may be categorized as high HRV. The HRV data corresponding to each low movement and high movement period may be continuously gathered and stored so that the HRV data may be used to determine the physical condition of the user (described in greater detail below).

According to various embodiments, operation 1335 of method 1300 includes determining the physical condition of the user by assessing the correlation of the generated heart rate data, motion data, and HRV data (operations 1305, 1315, and 1325). Determining the physical condition of the user may conclude that the user is currently stressed, relaxed, recovering, or exercising (described in further detail below). In a particular embodiment, the user's physical condition may be determined in pre-determined time intervals throughout the day (e.g., every 5 minutes, 10 minutes, 1 hour, 2 hour, etc.). The determined assessment of the user's physical condition may be stored and maintained in storage 1216 and/or storage 1226, or in cloud storage (e.g., in server 1206).

Furthermore, in some embodiments, the determined assessment of the user's physical condition may be displayed on a device platform, such as a computing device 1215. The determined physical condition of the user may be displayed in graphical form that depicts the biological and motion data collected from the activity monitoring devices (100, 800). In other embodiments, the device platform may provide a notification to inform the user his or her current physical condition throughout the day or provide a summary of the user's prior physical condition history.

Figure 14:
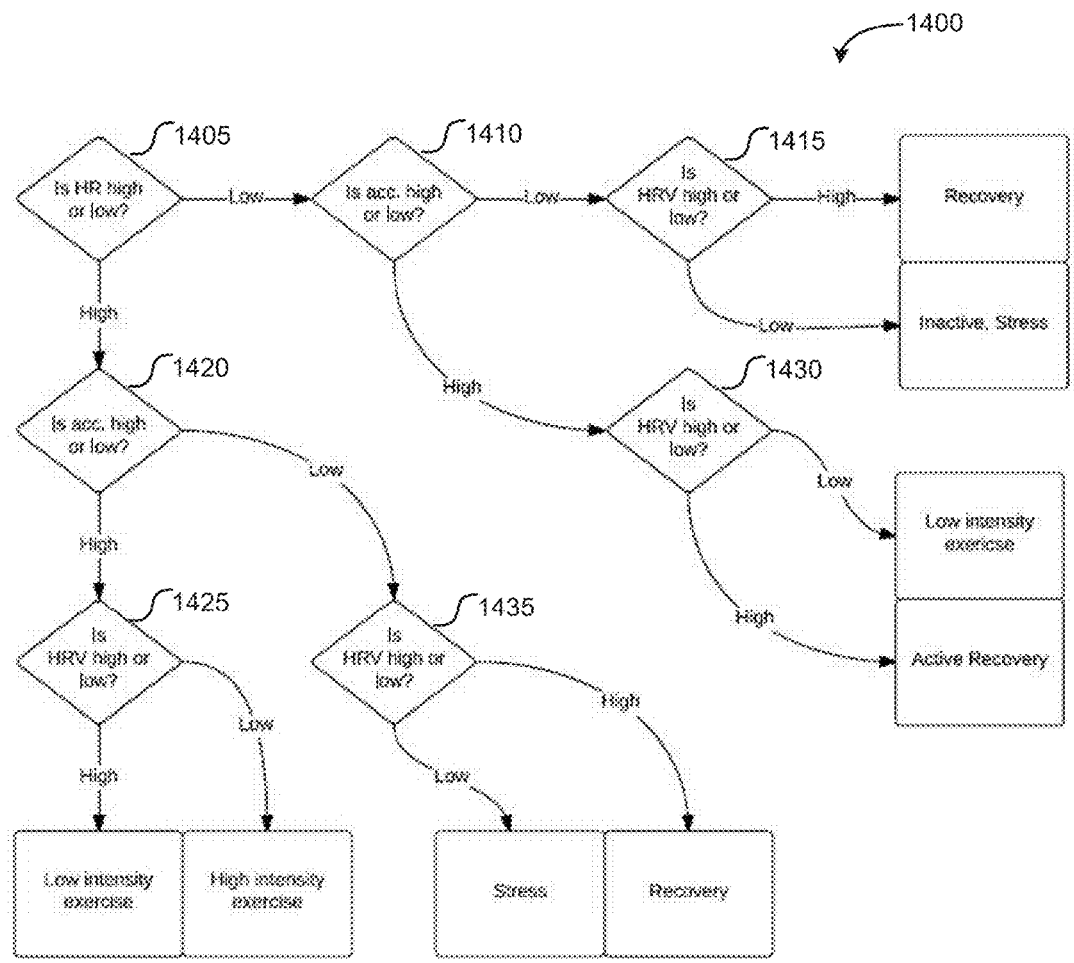
FIG. 14 is an example operational flow diagram illustrating various operations that may be performed to provide the current physical condition of the user, in accordance with various embodiments described herein.

FIG. 14 is an example flow diagram illustrating various operations to determine the user's physical condition, in accordance with various embodiments described herein. According to operation 1405 of method 1400, the generated heart rate data is gathered and assessed at each established time interval (e.g., every 30 seconds, every 5 minutes, every 1 hours, every 3 hours, etc.). to further categorize the heart rate data as high or low heart rate (operation 1310). The exemplary process may proceed to operation 1410 or 1420 to determine whether the motion data generated, or accelerometer movement monitored by the motion sensor, is categorized as high or low movement (operation 1320). In some embodiments, HRV data is optionally gathered at operation 1425, 1435, 1415, or 1430 to further categorize the HRV data as high or low HRV (operation 1330) for each high or low movement period associated with the corresponding motion data. Based on the aggregated heart rate data, motion data, and HRV data (optional), the user's corresponding physical condition may be determined.

In one particular embodiment, in the instance that the heart rate is categorized as low heart rate at operation 1405, the exemplary process proceeds to operation 1410 to determine whether the generated motion data is categorized as high or low (operation 1320). In the particular instance that the motion data is categorized as low, the exemplary process proceeds to operation 1415, where the HRV data corresponding to the low movement period from the motion data is gathered to determine whether the HRV data is categorized as low or high HRV (operation 1330). In the instance that the HRV is categorized as high HRV with respect to the low movement period of the motion data (1410), the physical condition of the user is determined to be in a state of recovery. However, in the instance that HRV data is categorized as low HRV, at operation 1415, with respect to the low movement period of the motion data (1410), the physical condition of the user is determined to be in a state of inactive stress. In particular, inactive stress may indicate that the user is fatigued.

Referring back to operation 1410, in the instance that heart rate is categorized as low heart rate from the corresponding heart rate data and motion is categorized as high movement from the corresponding motion data, the exemplary process may proceed to operation 1430 to determine whether the HRV data is categorized as low or high HRV (operation 1330). In the instance that the HRV data is categorized as low HRV with respect to the high movement period of the motion data (operation 1410), the physical condition of the user is determined to be in a state of low intensity exercise. However, in the instance that the HRV data is categorized as high HRV at operation 1430 with respect to the high movement period of the motion data (operation 1410), the physical condition of the user may be determined to be in a state of active recovery. A state of active recovery may indicate that the user is currently undergoing low intensity exercise that is just sufficiently high enough to increase blood flow and enhance the clearance of enzymes responsible for muscle damage and residual muscle fatigue, such as the delayed onset of muscle soreness. Some examples of active recovery state may include jogging or swimming at a low intensity pace for a short duration to help speed muscle recovery and fatigue.

Referring back to operation 1405, in the instance that the heart rate data is categorized as high, the exemplary process proceeds to operation 1420 to determine whether the motion data is categorized as high or low movement for a particular time period (operation 1320). In the particular instance that the motion data is categorized as low movement, the exemplary process proceeds to operation 1435, where the HRV data corresponding to the low movement period from the motion data is gathered to determine whether the HRV data is categorized as high or low HRV (operation 1420). In the instance that the HRV data is categorized as high, the physical condition of the user is determined to be in a passive recovery state. A passive recovery state may indicate that the user is inactive and resting after performing strenuous physical activity. However, in the instance that at operation 1435 the HRV data is categorized as low HRV in relation to the low movement time period from the corresponding motion data, the physical condition of the user is determined to be in a state of stress.

Referring back to operation 1420, in the instance that the motion data is categorized as high movement, the exemplary process proceeds to 1425, where the HRV data corresponding to the high movement period from the corresponding motion data is gathered to determine whether the HRV data is categorized as high or low HRV. In the instance that the HRV data is categorized as high HRV (operation 1420), the physical condition of the user is determined to be in a current state of performing low intensity exercise. However, in the instance that the HRV data is categorized as low HRV (operation 1410), the physical condition of the user is determined to be in a current state of performing high intensity exercise.

In some embodiments, method 1400 need not include assessing HRV data to determine a user's physical condition. As such, in the instance that HRV data is not incorporated to determine a user's physical condition where the generated heart rate data at operation 1405 is categorized as low heart rate and the motion data is categorized as low movement at operation 1410, the user's physical condition may be determined to be in a state of recovery. However, in the instance that the heart rate at operation 1405 is categorized as low heart rate and the motion data is categorized as high movement at operation 1410, the user's physical condition may be determined to be in a current state of performing low intensity exercise.

Similarly, in the instance that heart rate data is categorized as high heart rate at operation 1405 and the motion data is categorized as low movement at 1420, the user's physical condition may be determined to be in state of stress. However, in the instance that the heart rate is categorized as high heart rate at operation 1405 and the motion data is categorized as high movement at operation 1420, the user's physical condition may be determined to be in a current state of performing low intensity exercise.

Based on the determined physical condition generated by method 1400, the user may be notified of his or her various physical conditions throughout the day. Accordingly, the user may also proceed to make adjustments to pursue more active exercise or rest based on the user's current physical condition in order to achieve a more well-balanced lifestyle and healthier body.

Figure 15:
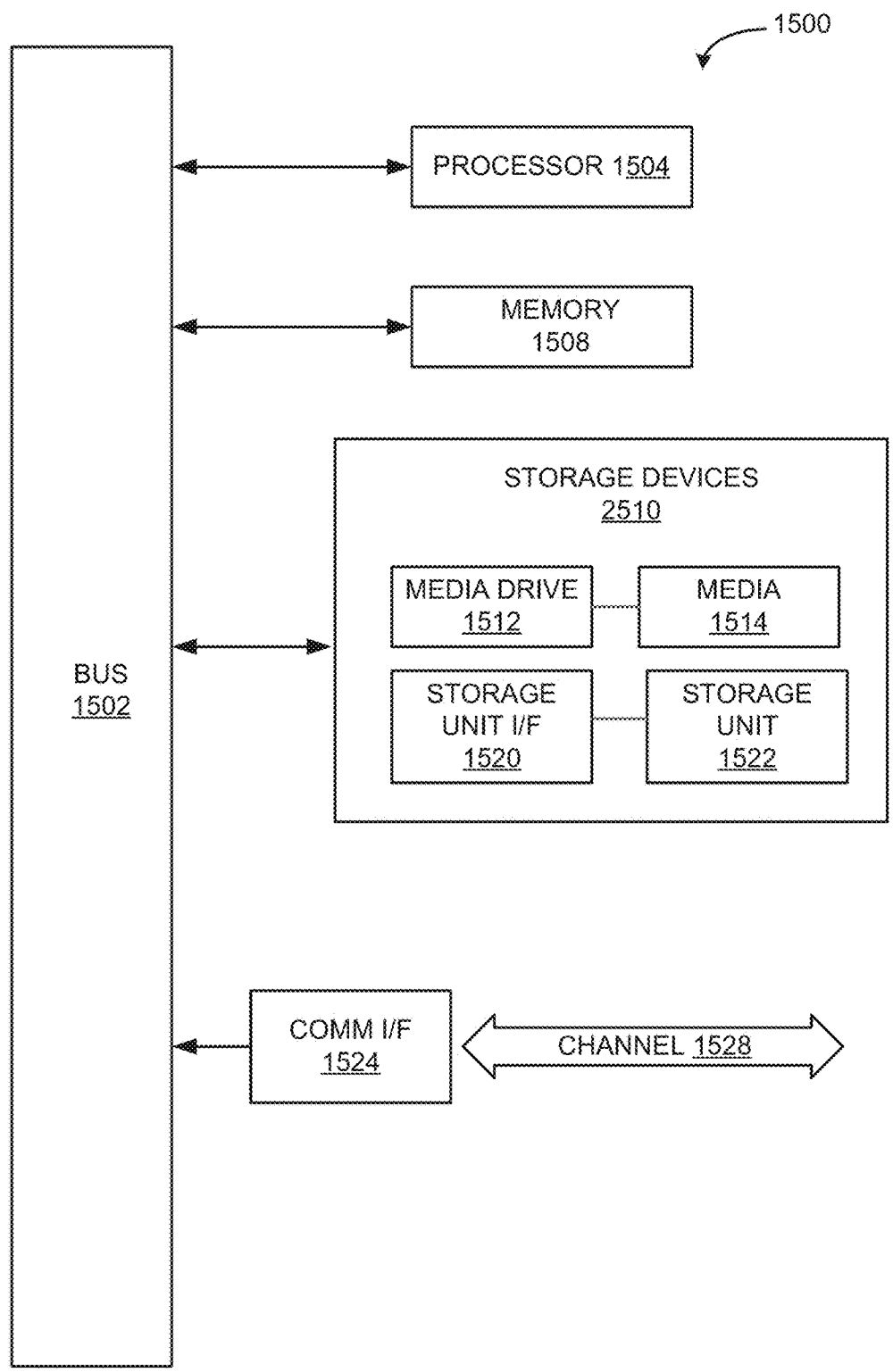
FIG. 15 illustrates an example computing module that may be used to implement various features of the technology disclosed herein.

FIG. 15 illustrates example computing module 1500, which may in some instances include a processor/controller resident on a computer system (e.g., computing device 1215 or wearable device 100). Computing module 1500 may be used to implement various features and/or functionality of embodiments of the systems and methods disclosed herein. With regard to the above-described embodiments of computing module 1500, computing device 1215, and wearable device 100, one of skill in the art will appreciate additional variations and details regarding the functionality of the embodiments, as set forth herein in the context of systems and method described with reference to FIGS. 1 through 14. In this connection, it will also be appreciated by one of skill in the art that features and aspects of the various embodiments (e.g., systems) described herein may be implemented with respected to other embodiments (e.g., methods) described herein without departing from the spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In implementation, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 14. Various embodiments are described in terms of example computing module 1400. After reading this description, it will become apparent to a person skilled in the relevant art how to implement the application using other computing modules or architectures.

Referring now to FIG. 15, computing module 1500 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing module 1500 is specifically purposed.

Computing module 1500 may include, for example, one or more processors, controllers, control modules, or other processing devices, such as a processor 1504. Processor 604 may be implemented using a special-purpose processing engine such as, for example, a microprocessor, controller, or other control logic. In the illustrated example, processor 1504 is connected to bus 1502, although any communication medium may be used to facilitate interaction with other components of computing module 1500 or to communicate externally.

Computing module 1500 may also include one or more memory modules, simply referred to herein as main memory 1508. For example, random access memory (RAM) or other dynamic memory may be used for storing information and instructions to be executed by processor 1504. Main memory 1508 may also be used for storing temporary variables or other intermediate information during execution of instructions to be executed by processor 1504. Computing module 1500 may likewise include a read only memory (ROM) or other static storage device coupled to bus 1502 for storing static information and instructions for processor 1504.

Computing module 1500 may also include one or more various forms of information storage devices 1510, which may include, for example, media drive 1412 and storage unit interface 1520. Media drive 1512 may include a drive or other mechanism to support fixed or removable storage media 1514. For example, a hard disk drive, a floppy disk drive, a magnetic tape drive, an optical disk drive, a CD or DVD drive (R or RW), or other removable or fixed media drive may be provided. Accordingly, removable storage media 1514 may include, for example, a hard disk, a floppy disk, magnetic tape, cartridge, optical disk, a CD or DVD, or other fixed or removable medium that is read by, written to or accessed by media drive 1512. As these examples illustrate, removable storage media 1514 may include a computer usable storage medium having stored therein computer software or data.

In alternative embodiments, information storage devices 1510 may include other similar instrumentalities for allowing computer programs or other instructions or data to be loaded into computing module 1500. Such instrumentalities may include, for example, fixed or removable storage unit 1522 and storage unit interface 1520. Examples of such removable storage units 1522 and storage unit interfaces 1520 may include a program cartridge and cartridge interface, a removable memory (for example, a flash memory or other removable memory module) and memory slot, a PCMCIA slot and card, and other fixed or removable storage units 1522 and storage unit interfaces 1520 that allow software and data to be transferred from removable storage unit 1522 to computing module 1500.

Computing module 1500 may also include a communications interface 1524. Communications interface 1524 may be used to allow software and data to be transferred between computing module 1500 and external devices. Examples of communications interface 1524 include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1524 may typically be carried on signals, which may be electronic, electromagnetic (which includes optical) or other signals capable of being exchanged by a given communications interface 1524. These signals may be provided to communications interface 1524 via channel 1528. Channel 1528 may carry signals and may be implemented using a wired or wireless communication medium. Some non-limiting examples of channel 1528 include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 1508, storage unit interface 1520, removable storage media 1514, and channel 1528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing module 1500 or a processor to perform features or functions of the present application as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. A system for determining a user's physical condition, the system comprising a wearable device, comprising:
   a band comprising a bio sensor that measures cardiac cycle phase data and is configured to transmit information about the measured cardiac cycle phase data via one or more electronic signals;
   earphones comprising a bio sensor that measures cardiac cycle phase data and is configure to transmit information about the measured cardiac cycle phase data via one or more electronic signals;
   a motion sensor that monitors activity of the user, wherein the motion sensor is disposed in the band or the earphones;
   a processor operatively coupled to the bio sensor disposed in the band and the bio sensor disposed in the earphones and the motion sensor disposed in the band or the earphones, the processor configured to process the electronic signals generated by at least one of the bio sensors and the motion sensor; and
   a non-transitory computer-readable medium operatively coupled to the processor and storing instructions that, when executed, cause the processor to:
      generate heart rate data from the information about the cardiac cycle phase data measured by at least one of the bio sensors;
      generate motion data from the activity monitored by the motion sensor and categorize the motion data as being one of high movement and low movement;
      calculate heart rate variability (HRV) data from the information about the cardiac cycle phase data measured by at least one of the bio sensors in the band or in the earphones; and
      determine a current state of the user's physical condition based on one or more of the heart rate data, motion data, and calculated HRV, wherein the determined current state of the user's physical condition includes recovery, wherein the recovery state is determined to occur at the time when the user has a calculated high HRV during a period where the generated motion data is categorized as low movement.

2. The system of claim 1, further comprising a smartphone, a tablet or a smartwatch, wherein the processor and the non-transitory computer-readable medium are disposed in the smartphone, the tablet, or the smartwatch.

3. The system of claim 1, wherein the bio sensor of the band or the earphones comprises at least one of a finger bio sensor that measures the, cardiac cycle phase data or a wrist bio sensor that measures the cardiac cycle phase data.

4. The system of claim 3, wherein the bio sensor is an optical heartrate sensor and is disposed in the band, and the optical heartrate sensor of the bio sensor continuously measures the cardiac cycle phase data.

5. The system of claim 1, wherein the motion data and the cardiac cycle phase data are measured at pre-determined time intervals throughout a day.

6. The system of claim 1, wherein the processor aggregates the motion data to classify the motion data into a category comprising high movement or low movement, wherein the motion data is further classified into user activities including sleeping, running, biking, swimming and walking.

7. The system of claim 6, wherein the processor calculates an HRV value from the cardiac cycle phase data, the processor aggregates the HRV values to classify the HRV values into a category comprising high HRV or low HRV with respect to the classified motion data.

8. The system of claim 1, wherein the instructions executed by the processor aggregates the heart rate data into a category comprising high heart rate or low heart rate.

9. The system of claim 1, wherein the non-transitory computer-readable medium stores further instructions, that when executed, cause the processor to determine the user's physical condition in pre-determined time intervals throughout a day.

10. The system of claim 1, further comprising a device platform, and wherein the non-transitory computer readable medium stores further instructions, that when executed, causes the processor to display the determined physical condition of the user on the device platform.

11. The system of claim 1, wherein the motion sensor is an accelerometer.

12. A computer-implemented method for determining a user's physical condition, the method comprising:
   measuring a user's cardiac cycle phase data using a bio sensor embedded in a wearable band and using a bio sensor embedded in earphones;
   generating heart rate data from the user's cardiac cycle phase data measured by at least one of the bio sensor embedded in the band or the bio sensor embedded in the earphones;
   generating motion data from an activity monitored by a motion sensor and categorizing the motion data as being one of high movement and low movement;

calculating HRV data from the user's cardiac cycle phase data measured by the at least one of the bio sensor embedded in the band and the bio sensor embedded in the earphones; and determining a user's physical condition based on one or more of the heart rate data, motion data, and the HRV data, wherein the user's physical condition includes recovery, wherein the recovery is determined to occur at the time when the user has a calculated high HRV during a period where the generated motion data is categorized as low movement.

13. The computer-implemented method of claim 12, wherein determining the user's physical condition further comprises capturing the motion data, heart data, and the HRV data continuously for an extended period of time.

14. The computer-implemented method of claim 12, wherein determining the user's physical condition further comprises capturing the motion data, heart rate data, and the HRV data in pre-determined time intervals for an extended period of time.

15. The computer-implemented method of claim 12, wherein determining the user's physical condition further comprises displaying the determined physical condition of the user on a device platform notifying the user's determined current physical condition or summarizing the user's determined past physical condition history.

* * * * *